(12) United States Patent
Canady et al.

(10) Patent No.: US 11,583,554 B2
(45) Date of Patent: Feb. 21, 2023

(54) COLD ATMOSPHERIC PLASMA THERAPY TO TREAT CANCER

(71) Applicant: Jerome Canady Research Institute for Advanced Biological and Technological Sciences, Takoma Park, MD (US)

(72) Inventors: Jerome Canady, Lakeland, FL (US); Xiaoqian Cheng, Fairfax, VA (US); Saravana Murthy, Owings Mills, MD (US); Taisen Zhuang, Rockvillle, MD (US)

(73) Assignee: Jerome Canady Research Institute, Takoma Park, MD (US)

( * ) Notice: Subject to any disclaimer, the term of this patent is extended or adjusted under 35 U.S.C. 154(b) by 128 days.

(21) Appl. No.: 17/133,101

(22) Filed: Dec. 23, 2020

(65) Prior Publication Data

US 2021/0187021 A1   Jun. 24, 2021

Related U.S. Application Data

(60) Provisional application No. 62/952,995, filed on Dec. 23, 2019.

(51) Int. Cl.
| | |
|---|---|
| *A61B 18/04* | (2006.01) |
| *A61K 35/16* | (2015.01) |
| *A61P 35/00* | (2006.01) |
| *G16B 50/30* | (2019.01) |

(52) U.S. Cl.
CPC .............. *A61K 35/16* (2013.01); *A61P 35/00* (2018.01); *G16B 50/30* (2019.02)

(58) Field of Classification Search
None
See application file for complete search history.

(56) References Cited

U.S. PATENT DOCUMENTS

| | | |
|---|---|---|
| 9,999,462 B2 | 6/2018 | Canady et al. |
| 10,023,858 B2 | 7/2018 | Canady et al. |
| 10,213,614 B2 | 2/2019 | Guron et al. |
| 10,329,535 B2 | 6/2019 | Trink et al. |
| 10,405,913 B2 | 9/2019 | Canady et al. |
| 2014/0378892 A1 | 12/2014 | Keidar et al. |
| 2017/0183631 A1 | 6/2017 | Keidar et al. |
| 2018/0117249 A1 | 5/2018 | Pennington |
| 2018/0271579 A1 | 9/2018 | Keidar et al. |
| 2019/0231411 A1* | 8/2019 | Canady ............... C12N 5/0093 |
| 2020/0060748 A1* | 2/2020 | Cheng ................. A61B 18/042 |
| 2020/0069355 A1* | 3/2020 | Keidar ................... A61N 2/002 |
| 2020/0069958 A1* | 3/2020 | Cheng ................. H05H 1/4652 |

FOREIGN PATENT DOCUMENTS

WO   2018191265 A1   10/2018

OTHER PUBLICATIONS

Graves, D. Low Temperature Plasma Biomedicine: A Tutorial Review Physics of Plasma 21(8)1-12, 2014. (Year: 2014).*
Russnes, H. G., Lingjaerde, O. C., Borresen-Dale, A.L. & Caldas, C., "Breast Cancer Molecular Stratification: From Intrinsic Subtypes to Integrative Clusters," Am J Pathol 187, 2152-2162 (2017).
Holliday, D. L. & Speirs, V.,"Choosing the right cell line for breast cancer research," Breast Cancer Research 13 (2011).
Hammond, M. E. et al., "American Society of Clinical Oncology/College Of American Pathologists guideline recommendations for immunohistochemical testing of estrogen and progesterone receptors in breast cancer," J Clin Oncol 28, 2784-2795, (2010).
Waks, et al. (Breast Cancer Treatment: A Review. JAMA 321, 288-300).
Howlader, N. et al., "US incidence of breast cancer subtypes defined by joint hormone receptor and HER2 status," J Natl Cancer Inst 106 (2014).
Adams, S. et al.,"Current Landscape of Immunotherapy in Breast Cancer: A Review," JAMA Oncol (2019).
Chernets, N., Kurpad, D. S., Alexeev, V., Rodrigues, D. B. & Freeman, T. A., "Reaction Chemistry Generated by Nanosecond Pulsed Dielectric Barrier Discharge Treatment is Responsible for the Tumor Eradication in the B16 Melanoma Mouse Model," Plasma Process Polym 12, 1400-1409 (2015).
Chen, Z. et al., "A Novel Micro Cold Atmospheric Plasma Device for Glioblastoma Both In Vitro and In Vivo," Cancers (Basel) 9 (2017).
Utsumi, F. et al., "Effect of indirect nonequilibrium atmospheric pressure plasma on anti-proliferative activity against chronic chemo-resistant ovarian cancer cells in vitro and in vivo," PLoS One 8 (2013).
Xu, D. et al., "Systemic study on the safety of immuno-deficient nude mice treated by atmospheric plasma-activated water," Plasma Science and Technology 20 (2018).
Liu, J.-R. et al., "Low-temperature plasma induced melanoma apoptosis by triggering a p53/PIGs/caspase-dependent pathway in vivo and in vitro," Journal of Physics D: Applied Physics 52 (2019).
Freund, E. et al., "Physical plasmatreated saline promotes an immunogenic phenotype in CT26 colon cancer cells in vitro and in vivo," Sci Rep 9, 634 (2019).
Rowe, W. et al., "The Canady Helios Cold Plasma Scalpel Significantly Decreases Viability in Malignant Solid Tumor Cells in a Dose-Dependent Manner," Plasma 1, 177-188 (2018).
Cheng, X. et al., "Treatment of Triple-Negative Breast Cancer Cells with the Canady Cold Plasma Conversion System: Preliminary Results," Plasma 1, 218-228 (2018).
Kornberg, R. D. & Lorch, Y., "Twenty-five years of the nucleosome, fundamental particle of the eukaryote chromosome," Cell 98, 285-294 (1999).
Khorasanizadeh, S., "The nucleosome: from genomic organization to genomic regulation," Cell 116, 259-272 (2004).
Heintz, N., "The regulation of histone gene expression during the cell cycle," Biochim Biophys Acta 1088, 327-339 (1991).

(Continued)

*Primary Examiner* — Ralph J Gitomer

(74) *Attorney, Agent, or Firm* — 24Ip Law Group Usa, PLLC; Timothy DeWitt

(57) ABSTRACT

A method for treating cancer by treating target cancer cells with cold atmospheric plasma to induce apoptosis of the target cancer cells through the degradation of Histone RNA during S-phase induced by oxidation of RNA.

9 Claims, 19 Drawing Sheets

(56) References Cited

OTHER PUBLICATIONS

Marzluff, W. F. & Duronio, R. J., "Histone mRNA expression: multiple levels of cell cycle regulation and important developmental consequences," Curr Opin Cell Biol 14, 692-699 (2002).

Osley, M. A., "The regulation of histone synthesis in the cell cycle," Annu Rev Biochem 60, 827-861 (1991).

Stein, et al., "Transcriptional control of cell cycle progression: the histone gene is a paradigm for the G1/S phase and proliferation/differentiation transitions," Cell Biol Int 20, 41-49 (1996).

DeRan, et al., "Transcriptional activation of histone genes requires NPATdependent recruitment of TRRAP-Tip60 complex to histone promoters during the G1/S phase transition," Mol Cell Biol 28, 435-447 (2008).

Miele, A. et al., "HiNF-P directly links the cyclin E/CDK2/p220NPAT pathway to histone H4 gene regulation at the G1/S phase cell cycle transition," Mol Cell Biol 25, 6140-6153 (2005).

Fletcher, et al., "Purification and characterization of OTF-1, a transcription factor regulating cell cycle expression of a human histone H2b gene," Cell 51, 773-781 (1987).

Mei, Q. et al., "Regulation of DNA replication-coupled histone gene expression," Oncotarget 8, 95005-95022 (2017).

Zhao, J., "Coordination of DNA synthesis and histone gene expression during normal cell cycle progression and after DNA damage," Cell Cycle 3, 695-697 (2004).

Ye, X. et al. Defective S phase chromatin assembly causes DNA damage, activation of the S phase checkpoint, and S phase arrest. Mol Cell 11, 341-351 (2003).

Meeks-Wagner, D. & Hartwell, L. H. Normal stoichiometry of histone dimer sets is necessary for high fidelity of mitotic chromosome transmission. Cell 44, 43-52 (1986).

Dai, X., Cheng, H., Bai, Z. & Li, J. Breast Cancer Cell Line Classification and Its Relevance with Breast Tumor Subtyping. J Cancer 8, 3131-3141, (2017).

* cited by examiner

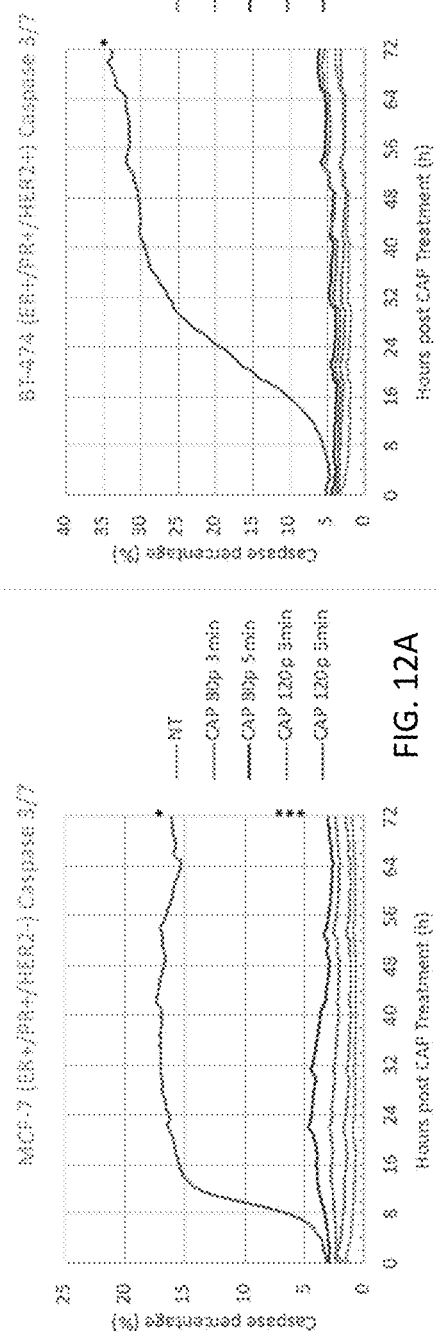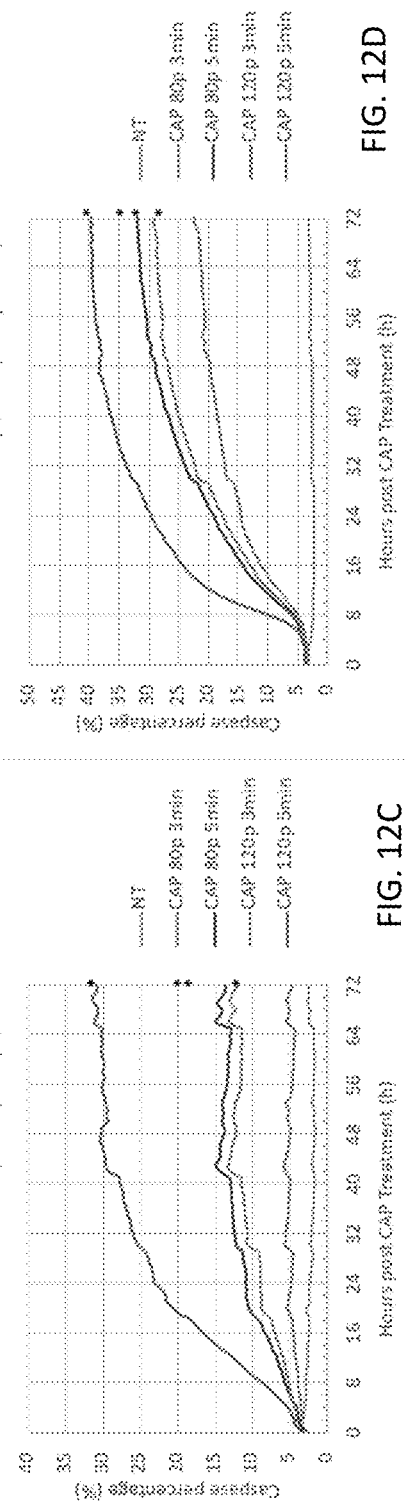

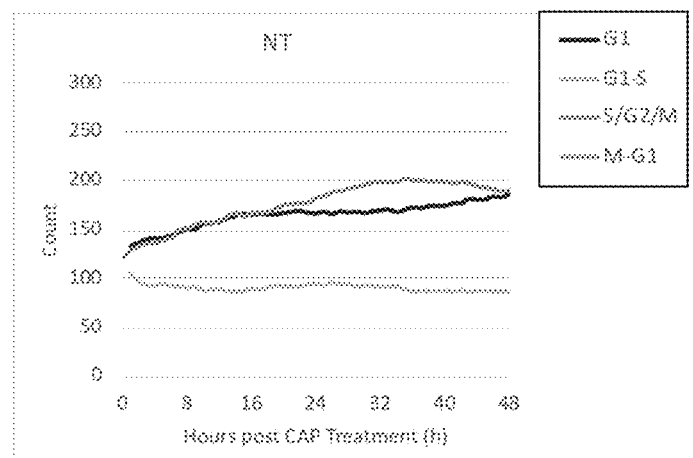
FIG. 18A
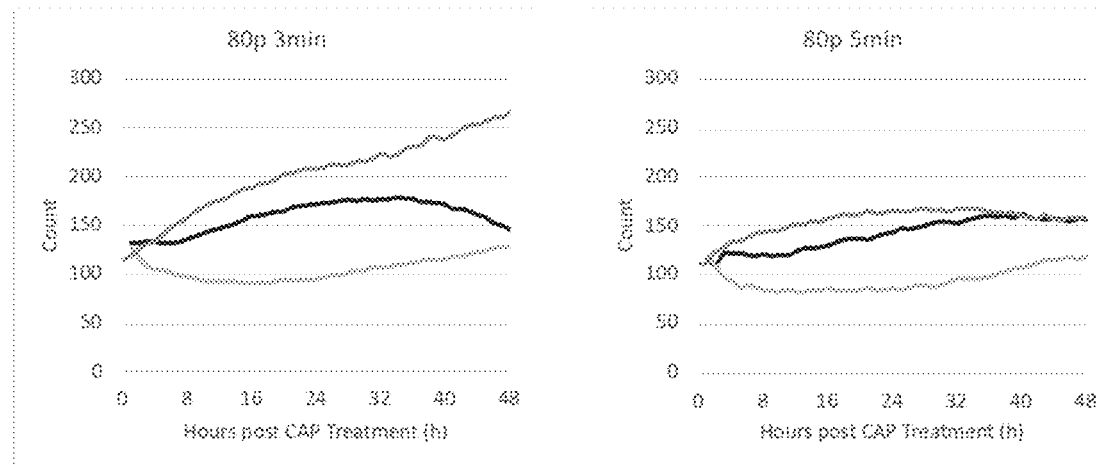
FIG. 18B
FIG. 18C
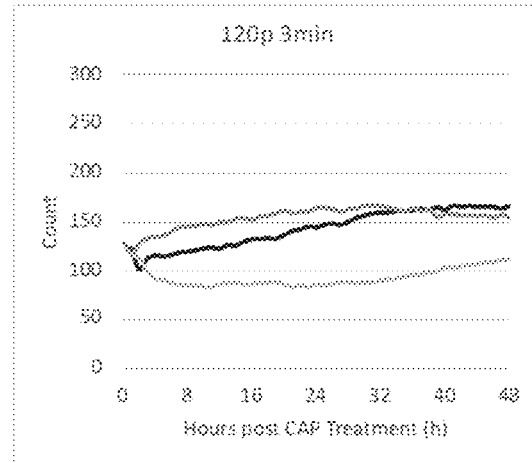
FIG. 18D
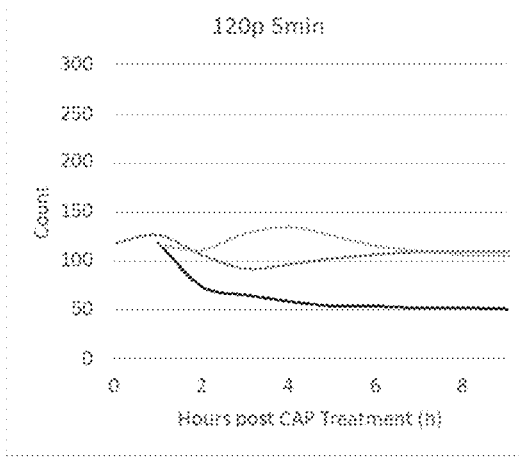
FIG. 18E

COLD ATMOSPHERIC PLASMA THERAPY TO TREAT CANCER

CROSS-REFERENCE TO RELATED APPLICATIONS

The present application claims the benefit of the filing date of U.S. Provisional Patent Application Ser. No. 62/952,995 filed by the present inventors on Dec. 23, 2019.

The aforementioned provisional patent application is hereby incorporated by reference in its entirety.

STATEMENT REGARDING FEDERALLY SPONSORED RESEARCH OR DEVELOPMENT

None.

BACKGROUND OF THE INVENTION

Field of the Invention

The present invention relates to systems and methods for treating cancer with cold atmospheric plasma.

Brief Description of the Related Art

Breast carcinomas can be categorized into different entities based on clinical behavior, histologic features, and/or by biological properties, which is important for the discovery of novel treatment, the study of tumor evolution, and the identification of mechanisms of treatment resistance. Russnes, H. G., Lingjaerde, O. C., Borresen-Dale, A. L. & Caldas, C., "Breast Cancer Molecular Stratification: From Intrinsic Subtypes to Integrative Clusters," *Am J Pathol* 187, 2152-2162 (2017). Molecular stratification based on gene expression profiling reveled that breast cancers could be classified into intrinsic subtypes including luminal A ($ER^+PR^{+/-}HER2^-$), luminal B ($ER^+PR^{-/-}HER2^+$), basal-like ($ER^-PR^-HER2^-$), and HER2-positive ($ER^-PR^-HER2^+$). Holliday, D. L. & Speirs, V., "Choosing the right cell line for breast cancer research," *Breast Cancer Research* 13 (2011); Dai, X., Cheng, H., Bai, Z. & Li, J. Breast Cancer Cell Line Classification and Its Relevance with Breast Tumor Subtyping. *J Cancer* 8, 3131-3141, (2017). HER2-positive breast cancer, for example, is a breast cancer that tests positive for a protein called human epidermal growth factor receptor 2 (HER2). This protein promotes the growth of cancer cells. Tumors with expression of either estrogen receptor (ER) or progesterone receptor (PR) in at least 1% of tumor cells are categorized as hormone receptor positive ($HR^+$). Hammond, M. E. et al., "American Society of Clinical Oncology/College Of American Pathologists guideline recommendations for immunohistochemical testing of estrogen and progesterone receptors in breast cancer," *J Clin Oncol* 28, 2784-2795, (2010).

Current approaches to the systemic and local treatment were reviewed by Waks, et al. (Breast Cancer Treatment: A Review. *JAMA* 321, 288-300) for the 3 major breast cancer subtypes: $11R^+HER2^-$, $HER2^+$, and triple negative breast cancer (TNBC). About 70% of breast cancer cases are $HR^+HER2^-$(Howlader, N. et al., "US incidence of breast cancer subtypes defined by joint hormone receptor and HER2 status," *J Natl Cancer Inst* 106 (2014)), and the use of endocrine agents to downregulate ER signaling is the primary systemic therapy for this subtype of breast cancers. $HER2^+$breast cancer constitutes 15-20% of breast cancer cases, and approximately half of $HER2^+$cases are also $HR^+$. Patients with $HER2^+$breast cancer benefit from HER2 targeted therapy including anti-HER2 antibodies such as trastuzumab and pertuzumab, and small-molecule tyrosine kinase inhibitors such as lapatinib and neratinib. Endocrine therapy is given in addition if concurrent HR positivity. Basal-like (TNBC) makes up approximately 15% of breast cancer cases. The specific molecular pathophysiology of this subtype remains poorly understood. In March 2019 the Food and Drug Administration (FDA) granted an accelerated approval for the immunotherapy drug atezolizumab in combination with chemotherapy for the initial treatment with locally advanced or metastatic TNBC with positive programed cell death 1 ligand (PD-L1) expression. This combined therapy is the first FDA-approved regimen for breast cancer to include immunotherapy. Adams, S. et al., "Current Landscape of Immunotherapy in Breast Cancer: A Review," *JAMA Oncol* (2019).

Cold atmospheric plasma (CAP) as an anti-cancer therapy across various cancer types have been investigated for more than a decade. To date, CAP treatment has demonstrated its significant anti-cancer capability over 20 cancer types in vitro including melanoma, glioblastoma, leukemia, kidney, pancreatic, lung, liver, breast, prostate, colorectal cancer and so forth. In vivo studies of CAP on mice are also have emerged over the past 5 years. Direct treatment on the subcutaneous or intracranial tumor nodules with a CAP device (Chernets, N., Kurpad, D. S., Alexeev, V., Rodrigues, D. B. & Freeman, T. A., "Reaction Chemistry Generated by Nanosecond Pulsed Dielectric Barrier Discharge Treatment is Responsible for the Tumor Eradication in the B16 Melanoma Mouse Model," *Plasma Process Polym* 12, 1400-1409 (2015); Chen, Z. et al., "A Novel Micro Cold Atmospheric Plasma Device for Glioblastoma Both In Vitro and In Vivo," *Cancers (Basel)* 9 (2017)), or indirect treatment with CAP-activated medium/water (Utsumi, F. et al., "Effect of indirect nonequilibrium atmospheric pressure plasma on anti-proliferative activity against chronic chemo-resistant ovarian cancer cells in vitro and in vivo," *PLoS One* 8 (2013); Xu, D. et al., "Systemic study on the safety of immuno-deficient nude mice treated by atmospheric plasma-activated water," *Plasma Science and Technology* 20 (2018); Liu, J.-R. et al., "Low-temperature plasma induced melanoma apoptosis by triggering a p53/PIGs/caspase-dependent pathway in vivo and in vitro," *Journal of Physics D: Applied Physics* 52 (2019)) have both been demonstrated to effectively reduce tumor growth rate and induce cancer cell death. In addition, immune-system activation after CAP-treatment was observed in several studies. See, e.g., Freund, E. et al., "Physical plasma-treated saline promotes an immunogenic phenotype in CT26 colon cancer cells in vitro and in vivo," *Sci Rep* 9, 634 (2019). In addition to the promising data demonstrated in laboratories, several clinical applications or trials of CAP have been reported around the world. For example, the system disclosed in U.S. Pat. No. 9,999,462 has been demonstrated to effectively eliminate various types of solid tumors including renal, colorectal, pancreatic, ovarian, esophageal and breast carcinoma. See, Rowe, W. et al., "The Canady Helios Cold Plasma Scalpel Significantly Decreases Viability in Malignant Solid Tumor Cells in a Dose-Dependent Manner," *Plasma* 1, 177-188 (2018); Cheng, X. et al., "Treatment of Triple-Negative Breast Cancer Cells with the Canady Cold Plasma Conversion System: Preliminary Results," *Plasma* 1, 218-228 (2018).

The million-dollar question has been how CAP can effectively destroy cancer while keeping normal tissue intact. There is evidence that the reactive oxygen species (ROS) and reactive nitrogen species (RNS) composing the plasma cocktail play an important role, as well as the species generated in the liquid phase when they are in contact with cell culture medium or bodily fluid. These species generated by CAP can affect the cells or tissue in several ways such as inducing apoptosis, cell cycle arrest and DNA damage.

The important structural components of eukaryotic chromatin are the histone proteins, which play crucial roles in all cellular processes that involve chromosomal DNA, such as DNA replication, transcription, DNA repair, recombination, and chromosome segregation. Kornberg, R. D. & Lorch, Y., "Twenty-five years of the nucleosome, fundamental particle of the eukaryote chromosome," *Cell* 98, 285-294 (1999); Khorasanizadeh, S., "The nucleosome: from genomic organization to genomic regulation," *Cell* 116, 259-272 (2004). Their assembly into chromosomes and their biosynthesis are tightly regulated with DNA synthesis during the S phase of the cell cycle and their regulation occur at both the transcriptional and the posttranscriptional levels leading to several fold increase during S phase (Heintz, N., "The regulation of histone gene expression during the cell cycle," Biochim *Biophys Acta* 1088, 327-339 (1991); Marzluff, W. F. & Duronio, R. J., "Histone mRNA expression: multiple levels of cell cycle regulation and important developmental consequences," *Curr Opin Cell Biol* 14, 692-699 (2002); Osley, M. A., "The regulation of histone synthesis in the cell cycle," *Annu Rev Biochem* 60, 827-861 (1991); Stein, et al., "Transcriptional control of cell cycle progression: the histone gene is a paradigm for the G1/S phase and proliferation/differentiation transitions," *Cell Biol Mt* 20, 41-49 (1996)) when regulatory proteins such as Oct1, OCA-S, HiNF-PYY1, NPA, HIRA, FLASH, and BZAP45 bind directly to the subtype-specific regulatory elements (SSREs) in the promoters region of the histone genes such as (H1, H2A, H2B, H3, and H4). DeRan, et al., "Transcriptional activation of histone genes requires NPAT-dependent recruitment of TRRAP-Tip60 complex to histone promoters during the G1/S phase transition," *Mol Cell Biol* 28, 435-447 (2008); Miele, A. et al., "HiNF-P directly links the cyclin E/CDK2/p220NPAT pathway to histone H4 gene regulation at the G1/S phase cell cycle transition," *Mol Cell Biol* 25, 6140-6153 (2005); Fletcher, et al., "Purification and characterization of OTF-1, a transcription factor regulating cell cycle expression of a human histone H2b gene," *Cell* 51, 773-781 (1987). Deregulation of histone genes leads to loss of chromosomes, DNA damage, and cell death. Mei, Q. et al., "Regulation of DNA replication-coupled histone gene expression," *Oncotarget* 8, 95005-95022 (2017); Zhao, J., "Coordination of DNA synthesis and histone gene expression during normal cell cycle progression and after DNA damage," *Cell Cycle* 3, 695-697 (2004); Ye, X. et al. Defective S phase chromatin assembly causes DNA damage, activation of the S phase checkpoint, and S phase arrest. *Mol Cell* 11, 341-351 (2003); Meeks-Wagner, D. & Hartwell, L. H. Normal stoichiometry of hi stone dimer sets is necessary for high fidelity of mitotic chromosome transmission. *Cell* 44, 43-52 (1986).

Several different systems and methods for performing Cold Atmospheric Plasma (CAP) treatment have been disclosed. For example, U.S. Pat. No. 10,213,614 discloses a two-electrode system for CAP treatment. U.S. Pat. Nos. 9,999,462 and 10,023,858 each disclose a converter unit for using a traditional electrosurgical system with a single electrode CAP accessory to perform CAP treatment. WO 2018191265A1 disclosed an integrated electrosurgical generator and gas control module for performing CAP.

SUMMARY OF THE INVENTION

Breast cancer is the most common cancer among women worldwide. It is a complex and heterogeneous disease that can be classified based on the status of molecular makers estrogen receptor (ER), progesterone receptor (PR) and human epidermal growth factor receptor 2 (HER2) into more sophisticated subtypes comprising luminal A ($ER^+ PR^{+/-} HER2^-$), luminal B ($ER^+PR^{+/-}HER2^+$), basal-like ($ER^-PR^-HER2^-$), and HER2-positive ($ER^-PR^-HER2^+$). To understand the cold atmospheric plasma (CAP) effect on breast cancer cell lines with different marker status, four breast cancer cell lines were tested with CAP with various power settings and treatment time. Differential progress of apoptosis on four breast cancer cell lines were induced by CAP in a dosage-dependent manner with each subtype required slightly different power or time settings to achieve 100% elimination. Inhibition of cell proliferation, induction of apoptosis, and arrest of cell cycle were observed when cells were monitored for up to 72 hours post CAP treatment. The data demonstrates for the first time that CAP is an effective approach for the treatment of breast cancer regardless of subtyping through the degradation of Histone RNA during S-phase induced by oxidation of RNA.

In a preferred embodiment, the present invention is a method for treating cancer by treating target cancer cells with cold atmospheric plasma to induce apoptosis of the target cancer cells through the degradation of Histone RNA during S-phase induced by oxidation of RNA.

In another preferred embodiment, the present invention is a method for performing cold atmospheric plasma therapy to treat cancer in a patient. The method comprises creating a database of cancer cell lines, associating with each cancer cell line in said database cold atmospheric plasma settings producing in each said cancer cell line degradation of Histone RNA during S-phase induced by oxidation of RNA, selecting on a graphical user interface of a cold atmospheric plasma generator a target cancer cell line to be treated, selecting with a processor in said cold atmospheric plasma generator cold atmospheric plasma settings associated with said target cancer cell line in said database stored, in a storage in said cold atmospheric plasma generator, and applying cold atmospheric plasma with said cold atmospheric plasma generator at said selected cold atmospheric pressure settings to said target cancer cells. The cancer being treated may be, for example, breast cancer.

Still other aspects, features, and advantages of the present invention are readily apparent from the following detailed description, simply by illustrating a preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description or may be learned by practice of the invention.

BRIEF DESCRIPTION OF THE DRAWINGS

For a more complete understanding of the present invention and the advantages thereof, reference is now made to the following description and the accompanying drawings, in which:

FIG. 7A shows viability assay was performed 48 hours post treatment. Data was normalized to control group (no treatment) of each cell line respectively. FIGS. 7B-7E shown confluence of MCF-7, BT-474, MDA-MB-231, and SK-BR-3 cells with or without CAP treatment over 72 hours. Student t test was performed on each treatment dosage and every hour post CAP treatment compared to NT (* $p<0.05$). NT=No Treatment; TNBC=Triple-negative breast cancer.

FIGS. 12A-12D show caspase 3/7 activity of breast cancer cell lines with or without CAP treatment over 72 hours A) MCF-7 (ER$^-$PR$^+$HER2$^-$). B) BT-474 (ER$^+$PR$^+$HER2$^+$). C) MDA-MB-231 (TN). D) SK-BR-3 (HER2$^+$).

FIG. 13A is a bar graph of averaged quantification plot of 'live', 'early apoptosis', and 'late apoptosis/dead' population of MCF-7 cells 24 h post CAP treatment. FIG. 13B is a bar graph of averaged quantification plot of 'live', 'early apoptosis', and 'late apoptosis/dead' population of MCF-7 cells 48 h post CAP treatment (* above the bars denotes statistical significance of CAP treated group compared to corresponding No Treatment group. * $p<0.05$,  $p<0.01$, and * $p<0.001$).

FIG. 14A is a bar graph of averaged quantification plot of 'live', 'early apoptosis', and 'late apoptosis/dead' population of BT-474 cells 24 h post CAP treatment. FIG. 14B is a bar graph of averaged quantification plot of 'live', 'early apoptosis', and 'late apoptosis/dead' population of BT-474 cells 48 h post CAP treatment (* above the bars denotes statistical significance of CAP treated group compared to corresponding No Treatment group. * $p<0.05$, $p<0.01$, and * $p<0.001$).

FIG. 14A is a bar graph of averaged quantification plot of 'live', 'early apoptosis', and 'late apoptosis/dead' population of MDA-MB-231 cells 24 h post CAP treatment. FIG. 14B is a bar graph of averaged quantification plot of 'live', 'early apoptosis', and 'late apoptosis/dead' population of MDA-MB-231 cells 48 h post CAP treatment (* above the bars denotes statistical significance of CAP treated group compared to corresponding No Treatment group; * between FIGS. 15C and 15D denotes statistical significance of the two groups. * $p<0.05$,  $p<0.01$, and * $p<0.001$).

FIG. 16A is a bar graph of averaged quantification plot of 'live', 'early apoptosis', and 'late apoptosis/dead' population of SK-BR-3 cells 24 h post CAP treatment. FIG. 16B is a bar graph of averaged quantification plot of 'live', 'early apoptosis', and 'late apoptosis/dead' population of SK-BR-3 cells 48 h post CAP treatment (* above the bars denotes statistical significance of CAP treated group compared to corresponding No Treatment group; * between FIGS. 16C and 16D denotes statistical significance of the two groups. * $p<0.05$,  $p<0.01$, and * $p<0.001$).

FIGS. 18A-18E show quantification of BT-474 (ER$^+$PR$^+$HER2$^+$) cells in G1, G1-S, S/G2/M, and M-G1 phases over 72 hours after CAP treatment. A-E) Cells were untreated or treated by CAP with various dosage.

DETAILED DESCRIPTION OF THE PREFERRED EMBODIMENTS

Breast cancer is the most common cancer among women worldwide. It is a complex and heterogeneous disease that can be classified based on the status of molecular makers estrogen receptor (ER), progesterone receptor (PR) and human epidermal growth factor receptor 2 (HER2) into more sophisticated subtypes comprising luminal A (ER$^+$PR$^{+/-}$HER2$^-$), luminal B (ER$^+$PR$^{+/-}$HER2$^+$), basal-like (ER$^-$PR$^-$HER2$^-$), and HER2-positive (ER$^-$PR$^-$HER2$^+$). To understand the cold atmospheric plasma (CAP) effect on breast cancer cell lines with different marker status, four breast cancer cell lines were tested with CAP with various power settings and treatment time. Differential progress of apoptosis on four breast cancer cell lines were induced by CAP in a dosage-dependent manner with each subtype required slightly different power or time settings to achieve 100% elimination. Inhibition of cell proliferation, induction of apoptosis, and arrest of cell cycle were observed when cells were monitored for up to 72 hours post CAP treatment. The data demonstrates for the first time that CAP is an effective approach for the treatment of breast cancer regardless of subtyping through the degradation of Histone RNA during S-phase induced by oxidation of RNA.

Figure 1:
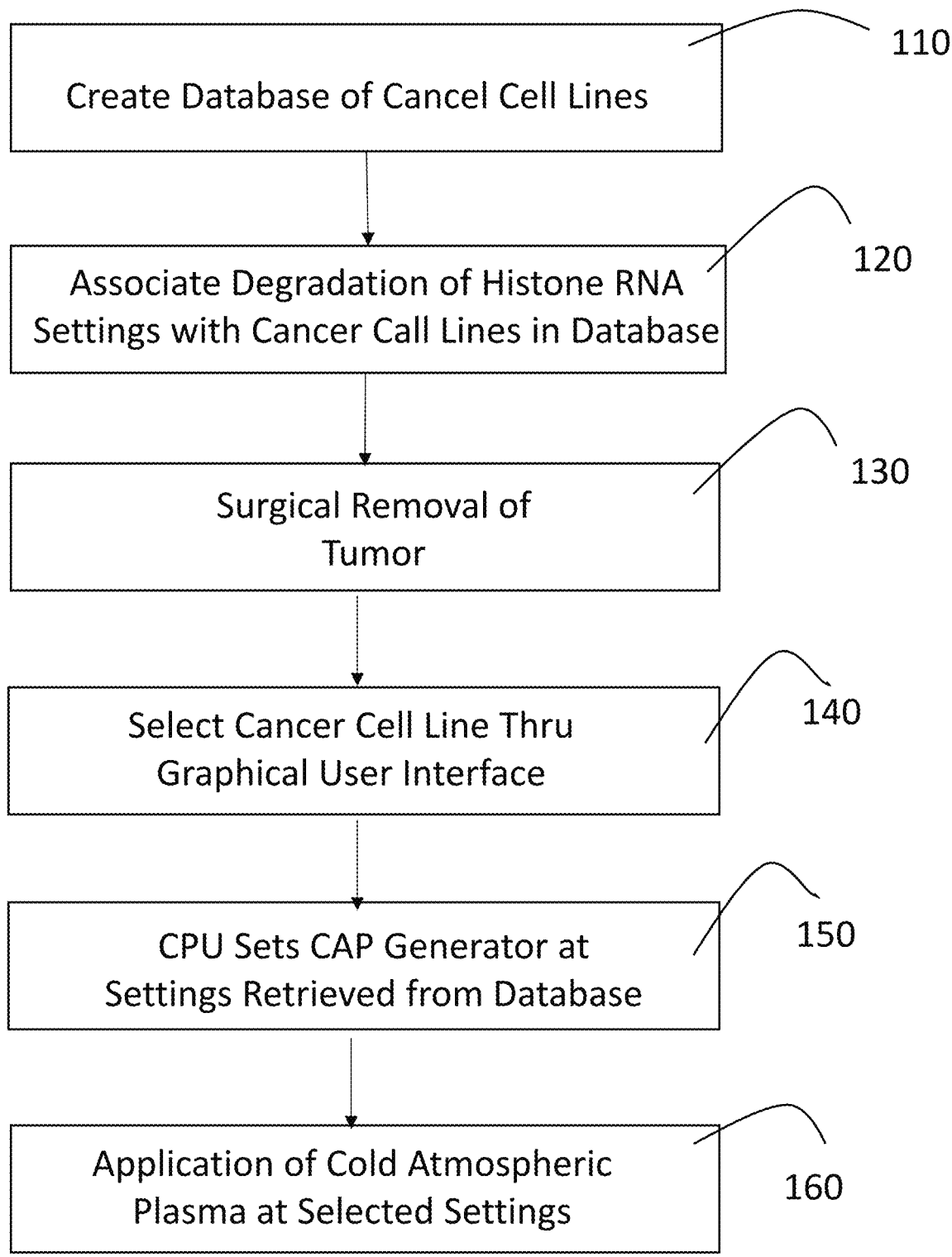
FIG. 1 is a flow diagram illustrating a method in accordance with a preferred embodiment of the present invention.

A method for treating breast cancer in accordance with a preferred embodiment of the present invention is shown in FIG. 1. A database of cancer cell lines is generated or created (110). Various cancer cell lines are tested to determine preferred CAP settings for producing degradation of hi stone RNA in the respective cancer cell lines. The preferred CAP settings are stored and associated with the respective cancer cell lines stored in the database (120). A cancerous tumor in a patient is tested to determine its corresponding cell line. The cancerous tumor is surgically removed (130). The type of cancer cell line is selected through a graphical user interface on a CAP generator (140). Settings for performing cold atmospheric plasma treatment on the particular cell line are retrieved from the database by a processor or CPU in the cold plasma generator (150). The margins surrounding the area where the cancerous tumor were removed are then treated with cold atmospheric plasma at the selected settings (160). A specific chemotherapy or radiation therapy may be given to the patient before, during or after the application of cold atmospheric plasma to reduce the cancer cells' resistance to cold atmospheric plasma therapy.

Figure 2:
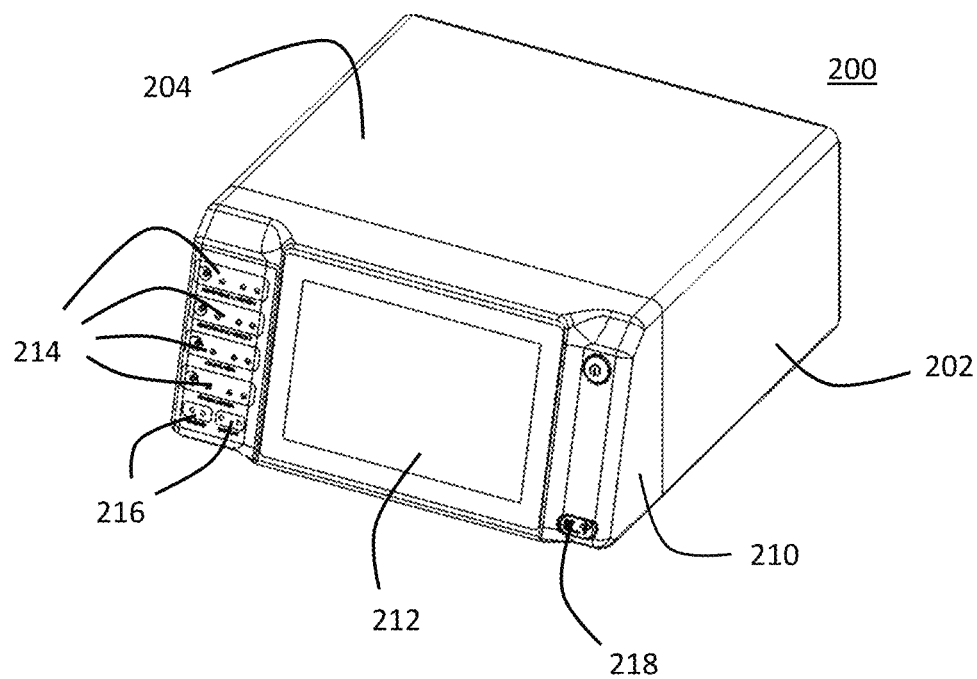
FIG. 2 is a perspective view of a preferred embodiment of a gas-enhanced electrosurgical generator that may be used in a preferred embodiment of the present invention.
Figure 3:
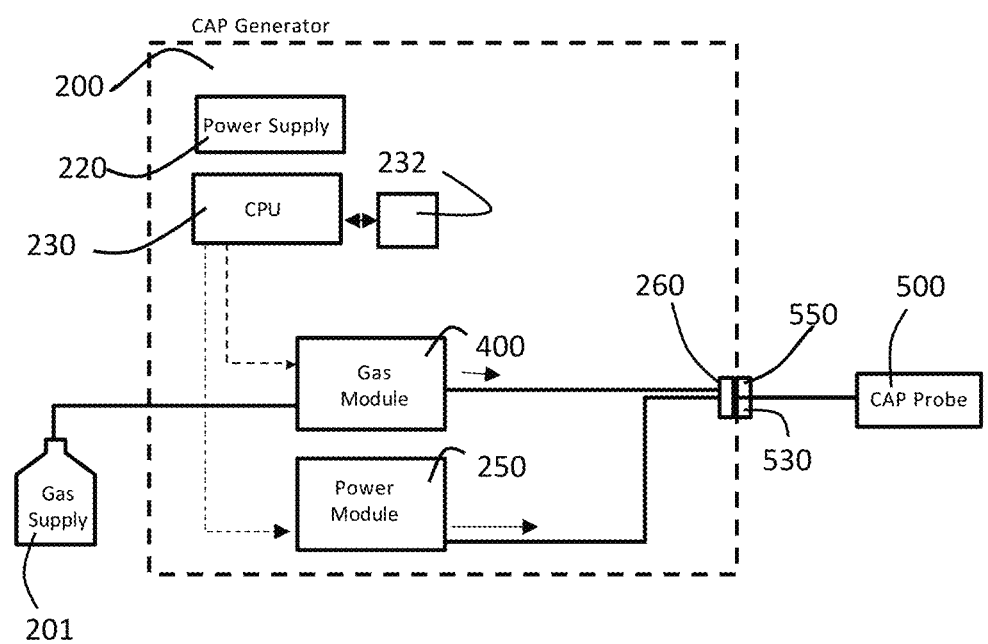
FIG. 3 is a block diagram of a cold atmospheric plasma generator in accordance with a preferred embodiment of the present invention.

A preferred embodiment of a CAP enabled generator is described with reference to the drawings. A gas-enhanced electrosurgical generator 200 in accordance with a preferred embodiment of the present invention is shown in FIGS. 2 and 3. The gas-enhanced generator has a housing 202 made of a sturdy material such as plastic or metal similar to materials used for housings of conventional electrosurgical generators. The housing 202 has a removable cover 204. The housing 202 and cover 204 have means, such as screws, tongue and groove, or other structure for removably securing the cover to the housing. The cover 204 may comprise just the top of the housing or multiple sides, such as the top, right side and left side, of the housing 202. The housing 202 may have a plurality of feet or legs (not shown) attached to the bottom of the housing. The bottom of the housing 202 may have a plurality of vents (not shown) for venting from the interior of the gas-enhanced generator.

A generator housing front panel 210 is connected to the housing 202. On the face front panel 210 there is a touch-screen display 212 and there may be one or a plurality of connectors 214 for connecting various accessories to the generator 200. For a cold atmospheric plasma generator such as is shown in FIG. 3, for example, there is a connector 260 for connecting a cold atmospheric probe 500. An integrated multi-function electrosurgical generator, such as is shown in FIG. 4B the plurality of connectors may include an argon plasma probe, a hybrid plasma probe, a cold atmospheric plasma probe, or any other electrosurgical attachment. The face of the front panel 210 is at an angle other than 90 degrees with respect to the top and bottom of the housing to provide for easier viewing and use of the touch screen display 212 by a user.

Figure 5:
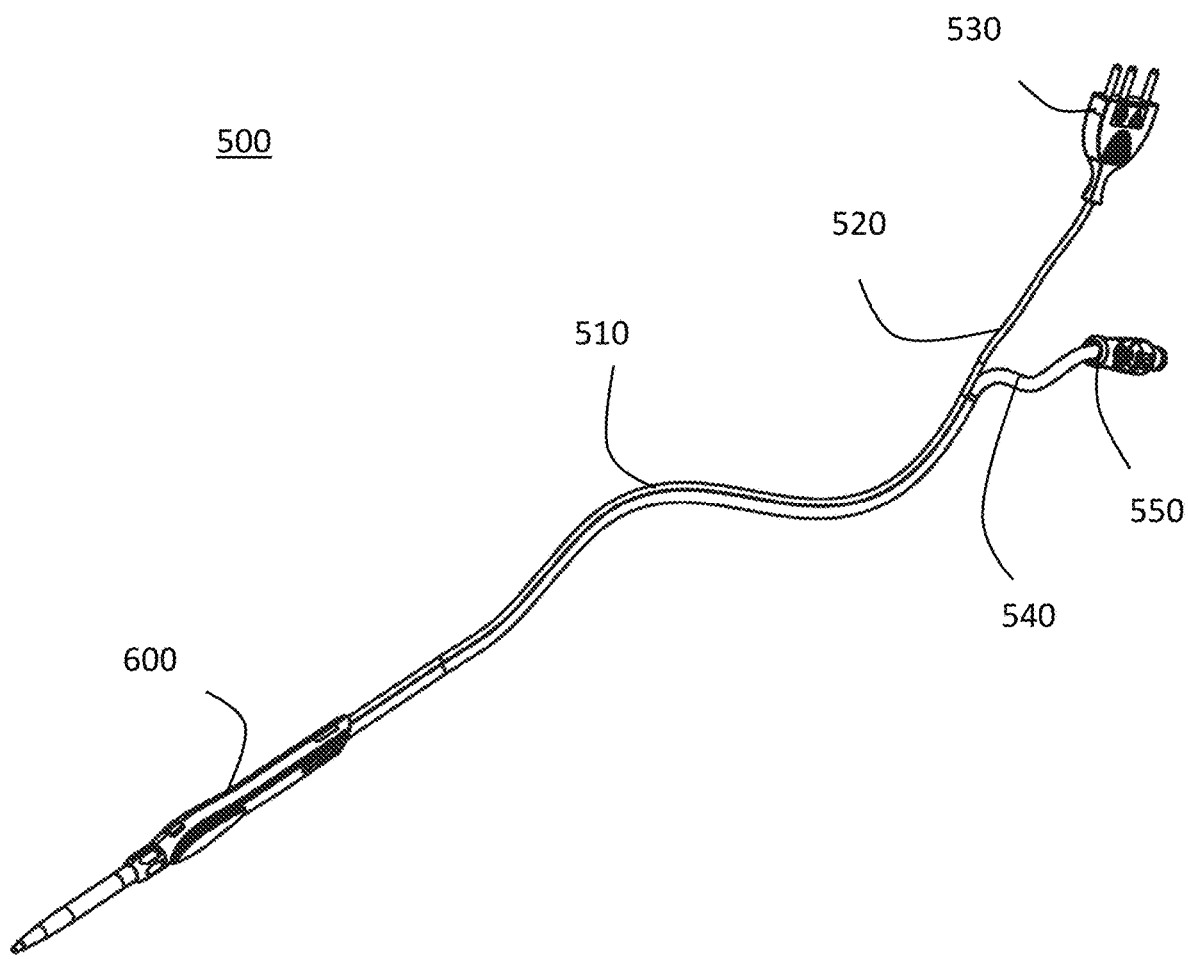
FIG. 5 is perspective view of a cold atmospheric plasma probe that may be used in a preferred embodiment of the present invention.
Figure 6A:
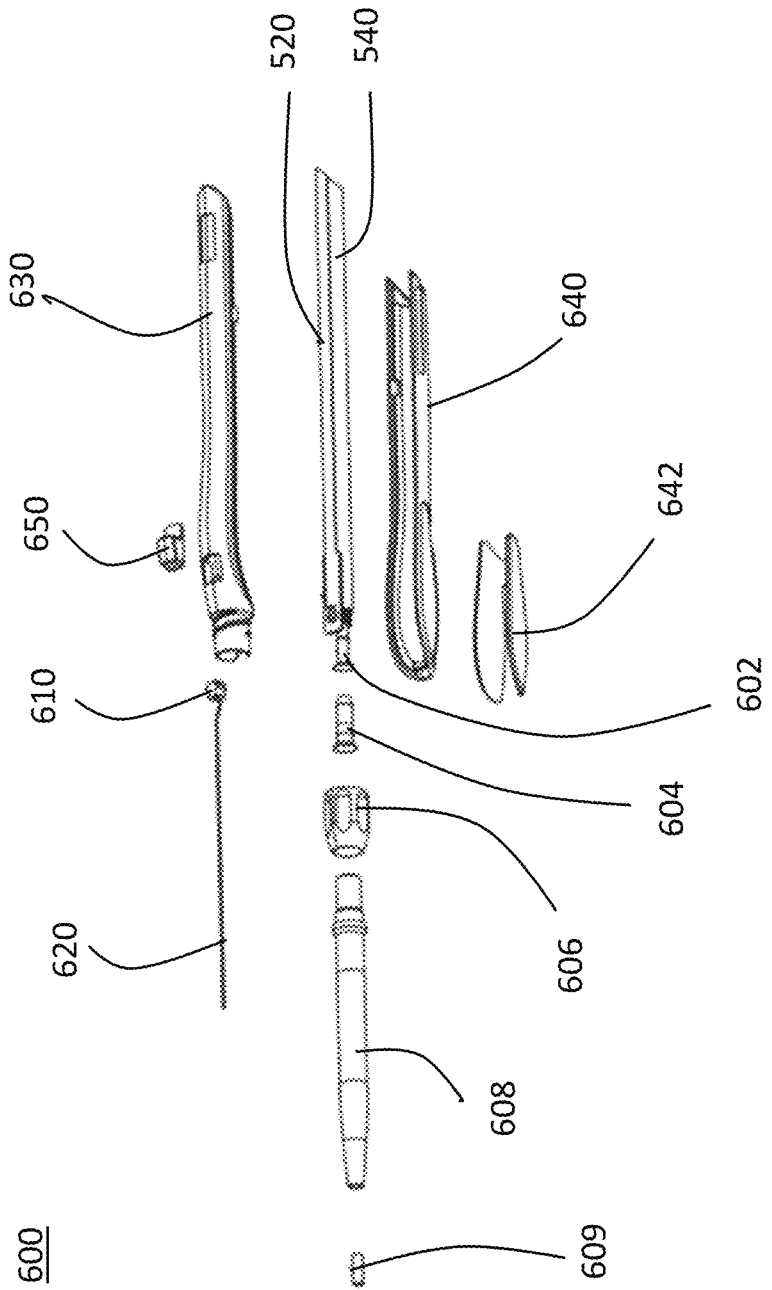
FIG. 6A is an assembly view of a handpiece of a cold atmospheric plasma probe that may be used in a preferred embodiment of the present invention.
Figure 6B:
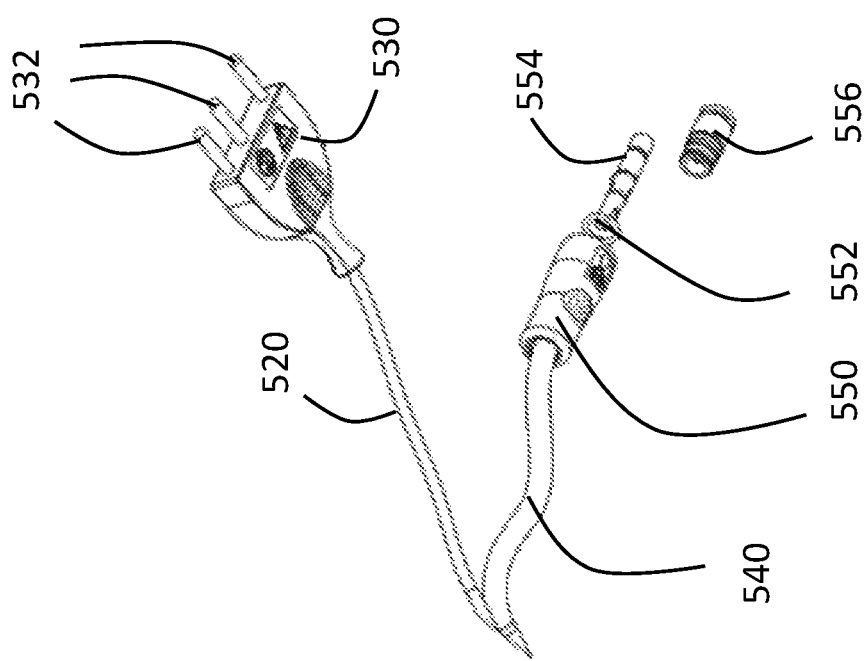
FIG. 6B is an assembly view of a cable harness of a cold atmospheric plasma probe that may be used in a preferred embodiment of the present invention.
Figure 7A:
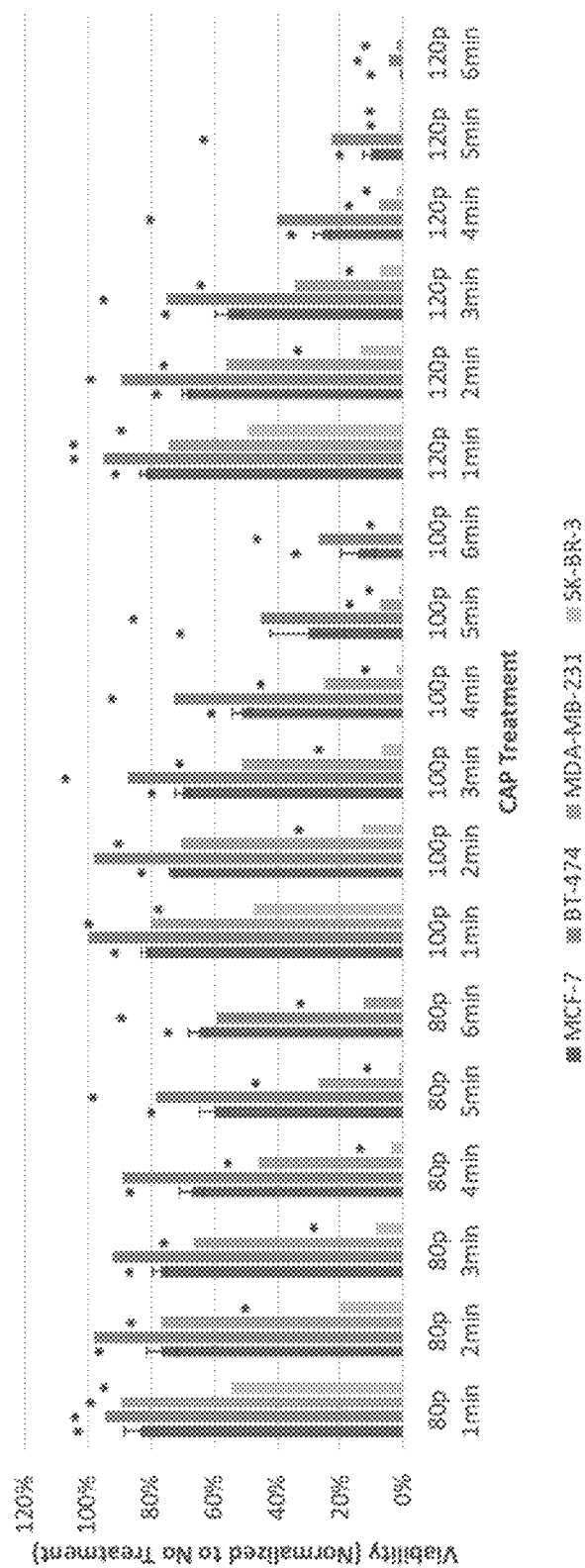
FIGS. 7A-7E are graphs showing viability of breast cancer cell lines after CAP treatment with various power and time settings.
Figure 7C:
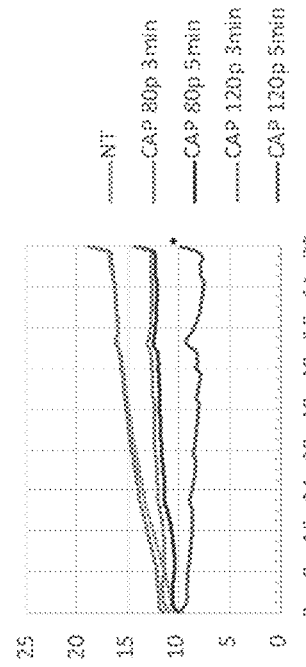
Figure 7E:
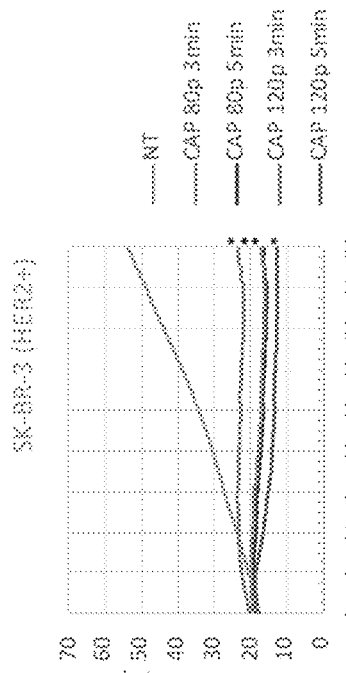
Figure 7B:
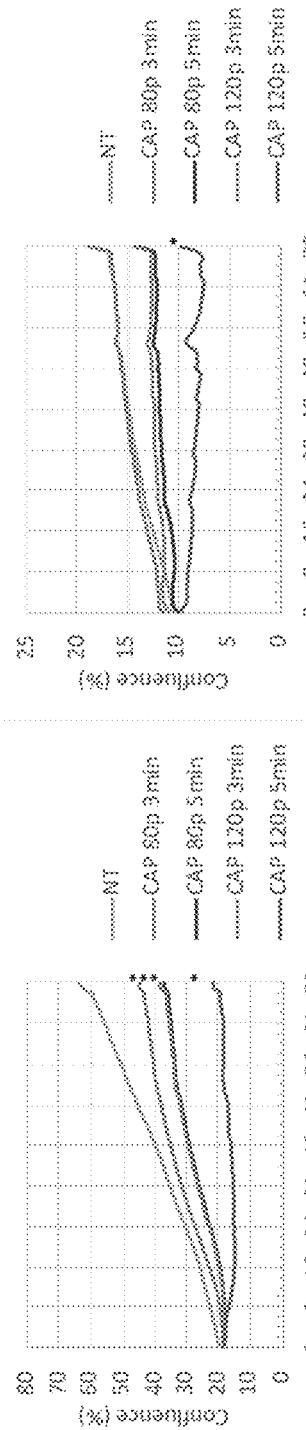
Figure 7D:
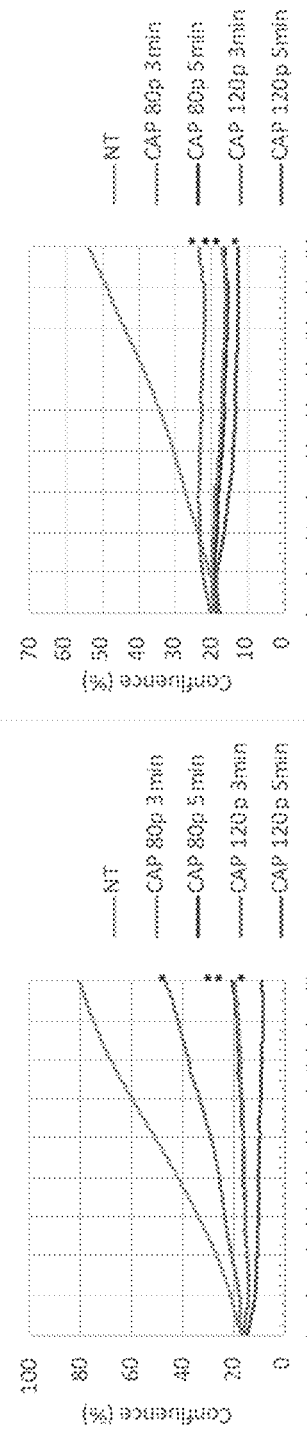

As shown in FIG. 3, an exemplary cold atmospheric plasma (CAP) generator 200 has a power supply 220, a CPU (or processor or FPGA) 230 and a memory or storage 232. The system further has a display 212 (FIG. 2), which may be the display of a tablet computer. The CPU 230 controls the system and receives input from a user through a graphical user interface displayed on display 212. The CAP generator further has a gas control module 400 connected to a source 201 of a CAP carrier gas such as helium. The gas control module 400 may be, for example, of the design described in International Patent Application No. WO 2018/191265, which is hereby incorporated by reference. The CAP generator 200 further has a power module 250 for generating low frequency radio frequency (RF) energy, such as is described in U.S. Pat. No. 9,999,462, which is hereby incorporated by reference in its entirety. The power module 250 contains conventional electronics and/or transformers such as are known to provide RF power in electrosurgical generators. The power module 250 operates with a frequency between 10-200 kHz, which is referred to herein as a "low frequency," and output peak voltage from 3 kV to 6 kV and preferably at a frequency near (within 20%) of 40 Hz, 100 Hz or 200 Hz. The gas module 400 and power module 250 are connected to connector 260 that allows for attachment of a CAP applicator 500 (as shown in FIGS. 5, 6A and 6B) to be connected to the generator 200 via a connector having an electrical connector 530 and gas connector 550.

As shown in FIG. 4B, other arrangements for delivery of the carrier gas and the electrical energy may be used with the invention. In FIG. 4B, an integrated CAP generator 300*b* is connected to a source 310 of a carrier gas (helium in this example), which is provided to a gas control system 400, which supplies the gas at a controlled flow rate to CAP applicator 500. A high frequency (HF) power module 340*b* supplies high frequency (HF) energy to a low frequency power module (converter) 350*b*, which outputs electrical energy having a frequency in the range of 10 kHz to 200 kHz and an output voltage in the range of 3 kV to 6 Kv. This type of integrated generator will have both a CAP connector 360*b* for connecting a CAP applicator or other CAP accessory and a connector 370*b* for attaching HF electrosurgical attachments such as an argon plasma or hybrid plasma probe (not shown).

Figure 4A:
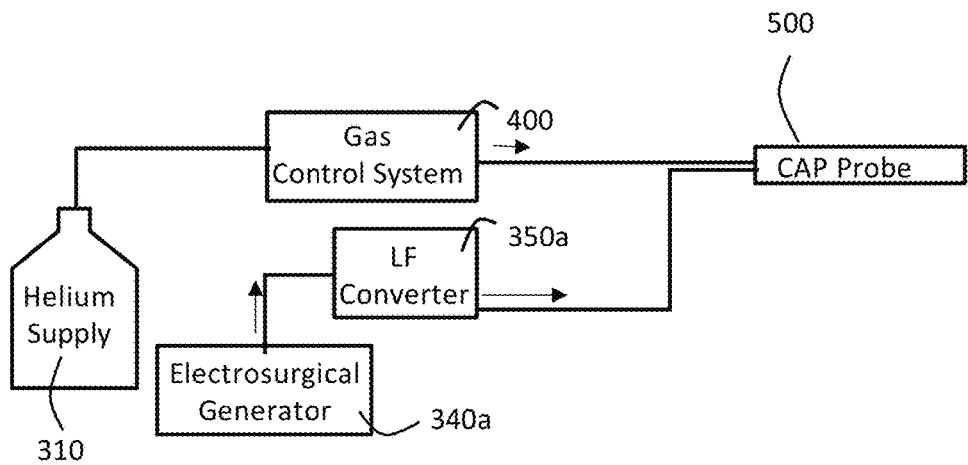
FIG. 4A is a block diagram of an embodiment of a cold atmospheric plasma system with an electrosurgical generator and a low frequency converter for producing cold plasma.
Figure 4B:
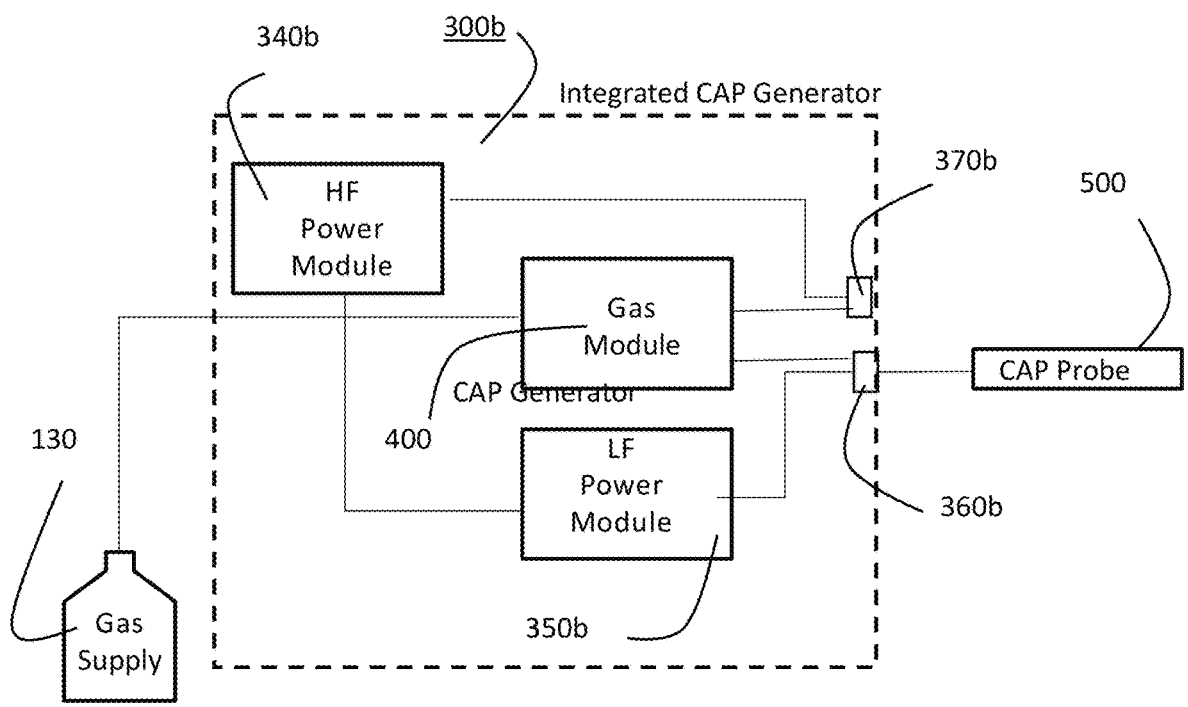
FIG. 4B is a block diagram of an embodiment of an integrated cold atmospheric plasma system that can perform multiple types of plasma surgeries.

Another embodiment, shown in FIG. 4A, has a carrier gas source 310 connected to a conventional gas control system 370, which in turn is connected to the CAP applicator 500, and a conventional electrosurgical generator 340 connected to a low frequency (LF) converter 350*a*, which is then connected to the CAP probe 500.

In the above-disclosed embodiment, a cold atmospheric plasma below 35° C. is produced. When applied to the tissue surrounding the surgical area, the cold atmospheric plasma induces metabolic suppression in only the tumor cells and enhances the response to the drugs that are injected into the patient.

The cold plasma applicator 500 may be in a form such as is disclosed in U.S. Pat. No. 10,405,913 and shown in FIGS. 5, 6A and 6B. A hand piece assembly 600 has a top side piece 630 and a bottom side piece 640. A control button 650 extends from the interior of the hand piece through an opening in the top side piece 630. Within the hand piece 600 is body connector funnel 602, PCB board 608, electrical wiring 520 and hose tubing (PVC medical grade) 540. The wiring 520 and hose tubing 540 are connected to one another to form a wire and tubing bundle 510. A grip over mold 642 extends over the bottom piece portion 640. In other embodiments, a grip may be attached to the bottom piece 640 in other manners. A probe or scalpel assembly is attached to the end of the hand piece. The probe assembly has non-bendable telescoping tubing 606, a ceramic tip 609, a column nut or collet 606 and body connector tubing 604. The hose tubing 540 extends out of the proximal end of the hand piece to a body gas connector 550, which has an O-ring 552, gas connector core 554 and gas connector tip 556 for connecting to a connector on a gas-enhanced electrosurgical generator. The printed circuit board 608 connects to electrical wiring 520 which leads to electrical connector 530 having electrical pins 532. Inside the handpiece 600 is an electrode 620 and conductive connector 610. There is a control button 650 for controlling the application of electrical energy.

Through experiments such as are described below, most-effective CAP settings can be determined with respect to various cancer cell lines based upon degradation of Histone RNA during S-phase induced by oxidation of RNA. Using results of such experiments, a database of most-effective settings and corresponding cancer cell lines can be generated and stored in the memory 232 of the CAP generator 200 or may be stored elsewhere and accessed by the CPU 230 in the generator. The graphical user interface on the touchscreen display 212 then may be used to select or enter a particular cancer cell line to cause the CAP generator to automatically select the preferred settings for performing CAP on a particular line of target cancer cells. The database further may include more complicated sets of data such as a type of chemotherapy or radiation therapy to be performed in conjunction with the application of CAP, for example, such that the CAP generator may select the appropriate CAP setting based upon the specific cancer cell line in combination with a type of other therapy being performed.

Experiments

Viability and Proliferation Reduction of Breast Cancer Cells after CAP Treatment Previous studies have suggested that CAP has anti-cancer effect in various cell lines. Despite the wide range of cold plasma generating devices being used worldwide, emerging evidence has shown that cell type-specific resistance can be observed in tumor cells. Conway, G. E. et al., "Non-thermal atmospheric plasma induces ROS-independent cell death in U373MG glioma cells and augments the cytotoxicity of temozolomide," *Br J Cancer* 114, 435-443 (2016). The inventors' study of CAP treatment on breast cancer cell lines, showed that CAP treatment can reduce breast cancer cell viability up to 92-99% based on receptor status. In present experiments, sensitivity of 4 breast cancer cell lines with different receptor status were compared and their apoptosis and cell cycle progress were observed.

Power- and time-dependent reduction in cell viability and proliferation rate of the 4 breast cancer cell lines was shown in FIGS. 7A-7E. The viability (FIG. 7A) of the CAP-treated cells was normalized to untreated cells 48-hour post CAP treatment. Increasing treatment time and power lead to lower cell viability across all 4 cell lines, among which SK-BR-3 ($ER^-PR^-HER2^+$) is the most sensitive to CAP treatment, and BT-474 ($ER^+PR^+HER2^+$) requires the strongest dosage. The viability established here provides an overview of each breast cancer subtype's reaction to CAP treatment under different settings. In the following experiments, four breast cancer cell lines were tested with 2 power settings (80 p and 120 p) for 3 treatment durations (3, 5, and 6 min) with helium flow rate set to 3 LPM.

Cells treated by CAP were incubated for 72 hours, then the confluence of the cells as an indicator for proliferation rate was analyzed and plotted by IncuCyte and shown in FIG. 7B-E. Student t test was performed on each treatment dosage and every hour post CAP treatment compared to NT, and * denotes statistical significance if $p<0.05$ during 48- to 72-hour post treatment. Compared to No Treatment (NT), CAP treatment reduced the growth of all cell lines to different extent based on the cell type and dosage. For BT-474 ($ER^+PR^+HER2^+$) cells (FIG. 7C), only with the highest dosage (CAP treatment with higher power and time i.e., 120 p 5 min) the cells started to show statistically significant decrease in confluence after 26 hours post treatment compared to NT. For MCF-7 ($ER^+PR^+HER2^-$), MDA-MB-231 (TNBC), and SK-BR-3 ($ER^-PR^-HER21$) cells (FIGS. 7B, D and E), proliferation rate decreased in a CAP power- and time-dependent manner: CAP treatment significantly slowed down MCF-7 cell proliferation but did not completely eliminate cells and they tended to recover after 48 hours of treatment; MDA-MD-231 cells was more responding to low dose CAP-treatment compared to BT-474 and MCF-7, and the highest dosage (120 p 5 min) was able to completely eradicated the cells; for SK-BR-3 ($ER^-PR^-HER21$) cells (FIG. 7E), all treatment dosages effectively stopped cell proliferation.

Cytotoxicity of CAP on breast cancer cells reducing cell proliferation was visualized by cell proliferation marker Ki-67. Differential Ki-67 expression can result in important therapeutic implications. Breast cancer cells were treated with desired CAP dosages and Ki-67/DAPI co-staining was performed 6, 24, or 48 hours post CAP treatment. Representative immunofluorescence images as well as quantification analysis were shown in FIG. 8 to FIG. 11. For quantification, Ki-67-positive (Ki-671 cell count was used instead of Ki-67$^+$cell percentage because the late apoptotic or dead cells were washed off during the staining process resulting in a false total cell count. Nuclei that were clearly in focus were outlined and its mean fluorescence intensity (MFI) of Ki-67 channel was recorded. The mean of Ki-67 MFI was calculated for each treatment group (5 images) including No Treatment and Isotype control. A Ki-67$^+$cell was defined as its Ki-67 MFI was greater than the lowest mean of MFI of all groups other than Isotype control for each cell line.

Figure 8:
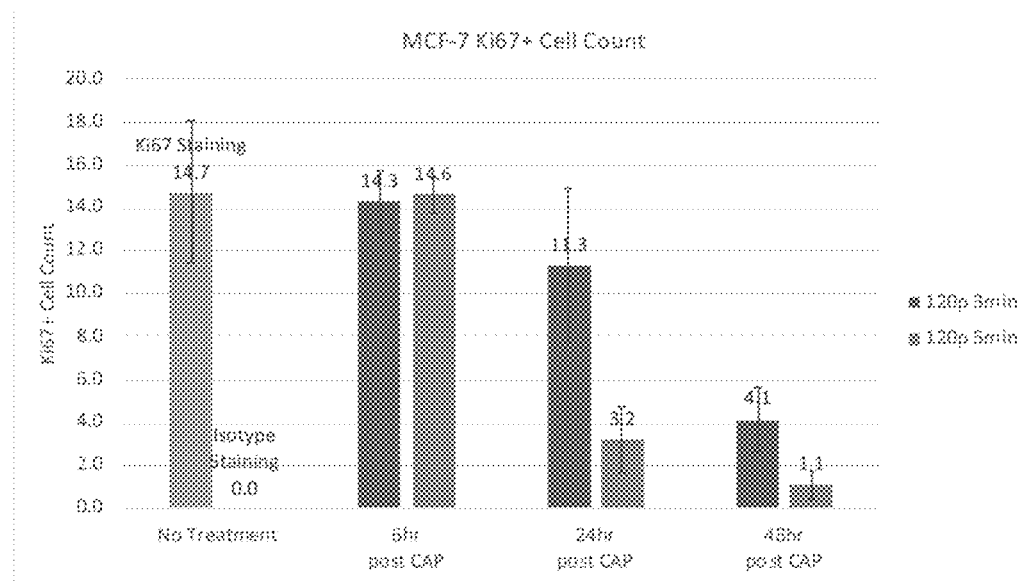
FIG. 8 is a bar graph of averaged quantification plot of 'Ki67$^{+}$' cell count of MCF-7 cells 6/24/48 h post CAP treatment (* above the bars denotes statistical significance of CAP treated group compared to No Treatment group. * $p<0.05$).
Figure 9:
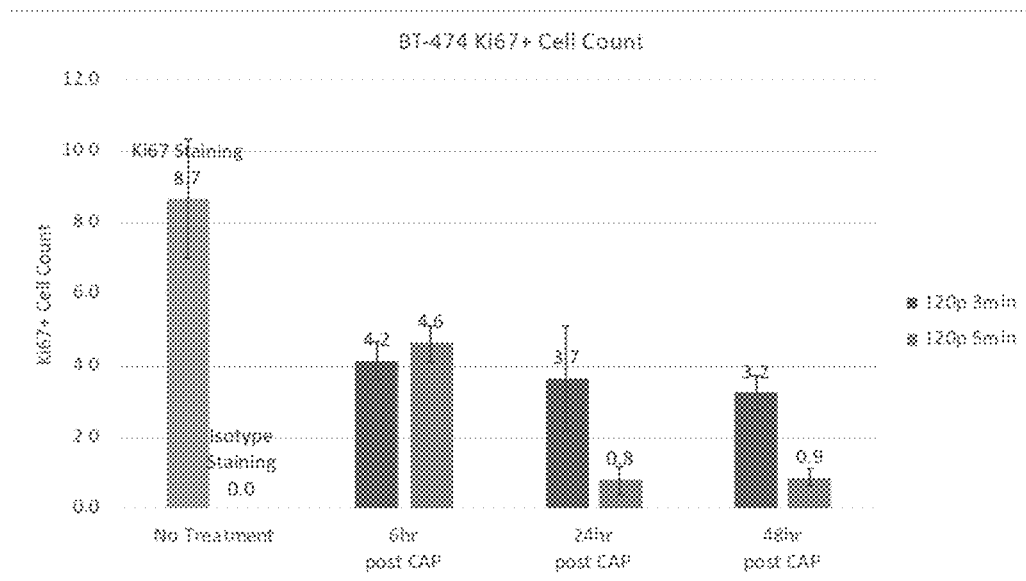
FIG. 9 is a bar graph of averaged quantification plot of 'Ki67$^{+}$' cell count of BT-474 cells 6/24/48 h post CAP treatment (* above the bars denotes statistical significance of CAP treated group compared to No Treatment group. * $p<0.05$).
Figure 10:
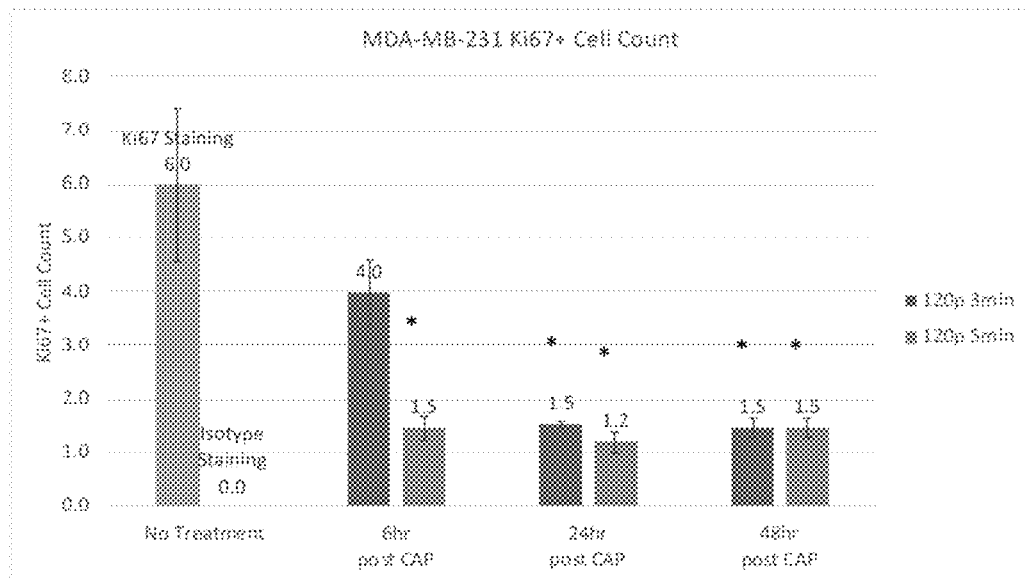
FIG. 10 is a bar graph averaged quantification plot of 'Ki67$^{+}$' cell count of MDA-MB-231 cells 6/24/48 h post CAP treatment (* above the bars denotes statistical significance of CAP treated group compared to No Treatment group. * $p<0.05$).
Figure 11:
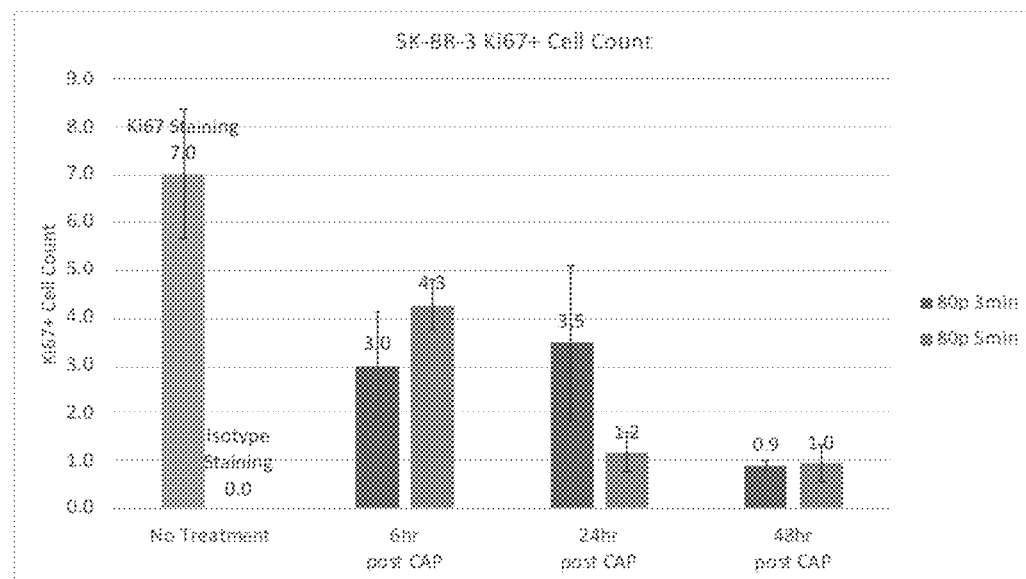
FIG. 11 is a bar graph of averaged quantification plot of 'Ki67$^{+}$' cell count of SK-BR-3 cells 6/24/48 h post CAP treatment (* above the bars denotes statistical significance of CAP treated group compared to No Treatment group. * $p<0.05$).
Figure 13A:
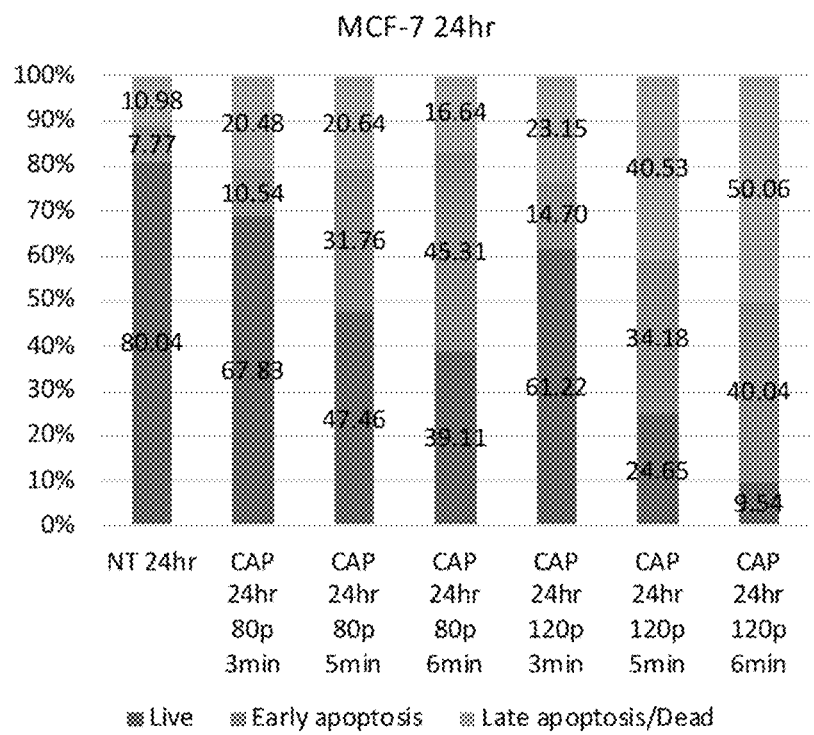
FIGS. 13A-13B show apoptosis analysis of MCF-7 (ER$^-$PR$^+$HER2$^-$) cell line.
Figure 13B:
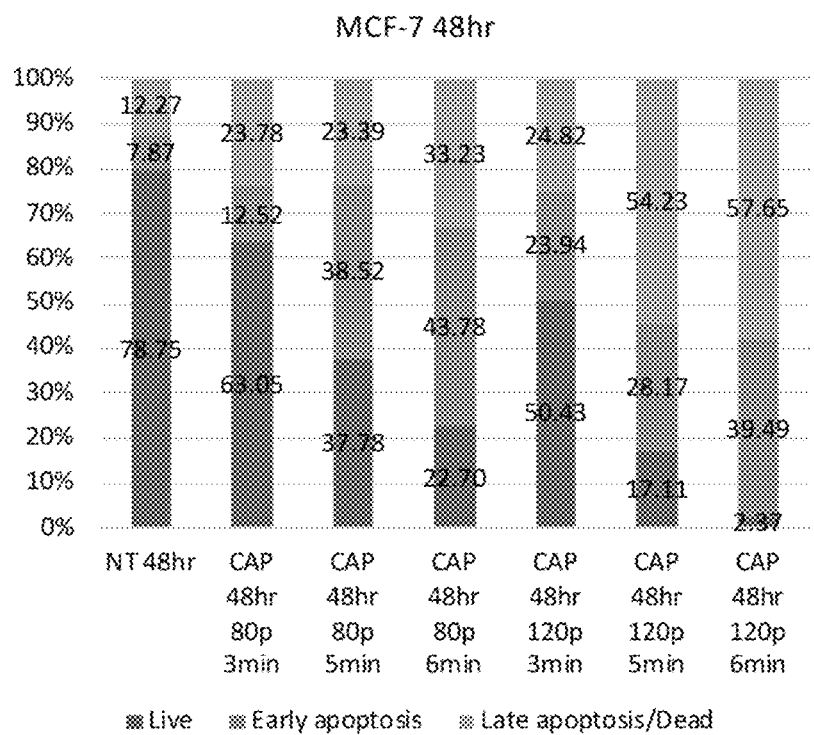

In the images (FIG. 8 to FIG. 11), Ki-67 staining was remarkably brighter in cells with No Treatment or with lower dosages of CAP than those treated with higher dosages. In MCF-7 ($ER^+PR^+HER2^-$) No treatment samples, Ki-67 was seen throughout the nucleoplasma, and in most cases in co-localization with nucleoli. At low dose or short incubation time (6 h 120 p 3 min, 6 h 120 p 5 min, 24 h 120 p 3 min, and 48 h 120 p 3 min), nucleoli were intact and Ki-67 expression was still observed but in less cells; at high dose (24 h 120 p 5 min and 48 h 120 p 5 min), Ki-67 staining was either diminished or presented throughout the nuclei with disrupted nucleoli. The same pattern was seen in all 4 breast cancer cell lines with slightly different treatment conditions. For MCF-7 ($ER^+PR^+HER2^-$), BT-474 ($ER^!PR^+HER2^+$), and MDA-MB-231 (TN), CAP treatment at 120 p 5 min caused visual damage to the nuclei after 24-hour incubation (FIG. 8 to FIG. 10). For SK-BR-3 ($HER2^+$), visual nuclear damage was observed as early as 6-hour post CAP treatment at a lower treatment dose of 80 p 3 min.

The number of Ki-67$^+$ cells was reduced by CAP treatment in all 4 breast cancer cell lines as a power- and time-dependent manner (FIG. 8 to FIG. 11). Over 6, 24, and 48 h incubation post CAP, the Ki-67$^+$cell number gradually decreased. In addition to the reduced Ki-67$^+$cell count, the shape and size of the nuclei changed after CAP treatment. Shrinkage and fragmentation were seen in all the cells treated with the highest dosage of CAP. The reduction in cell number correlates with the inhibition of growth observed in the viability and confluency in FIGS. 7A-7E.

Apoptosis of Breast Cancer Cells after CAP Treatment

The next question was whether CAP merely reduced cell proliferation or induced cell death. As an important step of downstream apoptosis pathway, caspase 3/7 activity was measured to understand the timeline of apoptotic activities for each cell line. After CAP treatment, cells were stained with IncuCyte® Caspase-3/7 Dyes for Apoptosis, put back immediately back to incubator and scanned with IncuCyte 10× lens for 3 days (0 to 72 hours post CAP). Phase contrast images were taken every 1 hour to monitor the progress of apoptosis. The percentage of caspase-3/7-active cells out of the total population per image from 0 to 72 hours post CAP treatment was analyzed by IncuCyte software and shown in FIGS. 12A-12D. In accordance with the viability data shown in FIGS. 7A-7E, compared to NT, significant apoptosis activity (* p<0.05) was observed in MCF-7 ($ER^+PR^+HER2^+$) MDA-MB-231 (TNBC), and SK-BR-3 ($ER^-PR^-HER2^+$) cells (FIGS. 12A, C, and D) by all CAP treatment doses, with SK-BR-3 ($ER^-PR^-HER2^+$, FIG. 12D) the most susceptible and MCF-7 ($ER^+PR^+HER2^-$, FIG. 12A) the most resistant. BT-474 ($ER^+PR^+HER2^+$) cells were the most robust among all the cell lines, but the highest dosage of CAP treatment (120 p 5 min) was able to result in statistically significant apoptosis in BT-474 ($ER^+PR^+HER2^+$) cells (FIG. 12B). For all four breast cancer cell lines, apoptosis (if induced by CAP) initiated within 4 hours post treatment and plateaued after 48 hours post treatment. For each cell line, the slope of the caspase 3/7 curve representing the kinetic of apoptotic activity is dose-dependent, suggesting that the higher CAP dose (higher power or longer duration), the earlier and faster apoptosis occurred.

The great advantage of IncuCyte live cell imaging is to monitor and visualize apoptosis progress continuously from Hour 0. However, the limitation of IncuCyte, as is to all 2-dimensional imaging analysis, is that the detached cells were not in the focal plane thus not in the analysis. To better quantify the apoptotic population and calculate the percentage of apoptosis, cells were stained with Annexin V vs. Propidium iodide (PI) staining and cell apoptosis at 24 and 48 post CAP treatment was confirmed by flow cytometry. Representative scatter and quantification plots of 'live', 'early apoptosis', and 'late apoptosis/dead' cells for each breast cancer cell line were shown in FIG. 13A to FIG. 16D.

For all 4 cell lines, in the No Treatment samples, the majority of cells (~80-90%) of cells were viable ('Live', Annexin In contrast, exposure to CAP treatment for 3, 5 or 6 min at 80p or 120p induced apoptosis to various extent over 24 and 48 hr incubation time.

Figure 14A:
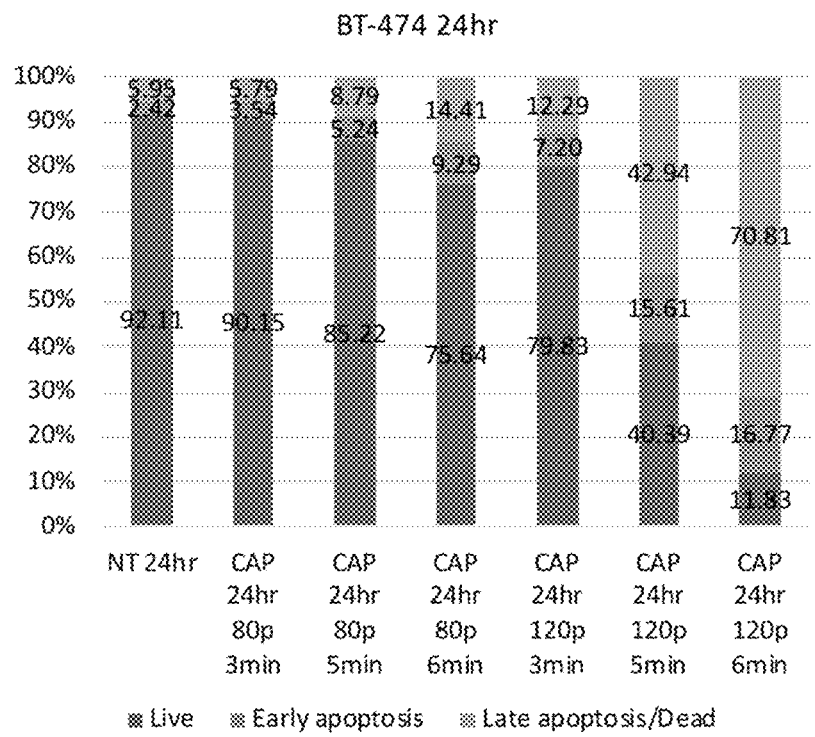
FIGS. 14A-14B show an apoptosis analysis of BT-474 (ER$^-$PR$^+$HER2$^-$) cell line.
Figure 14B:
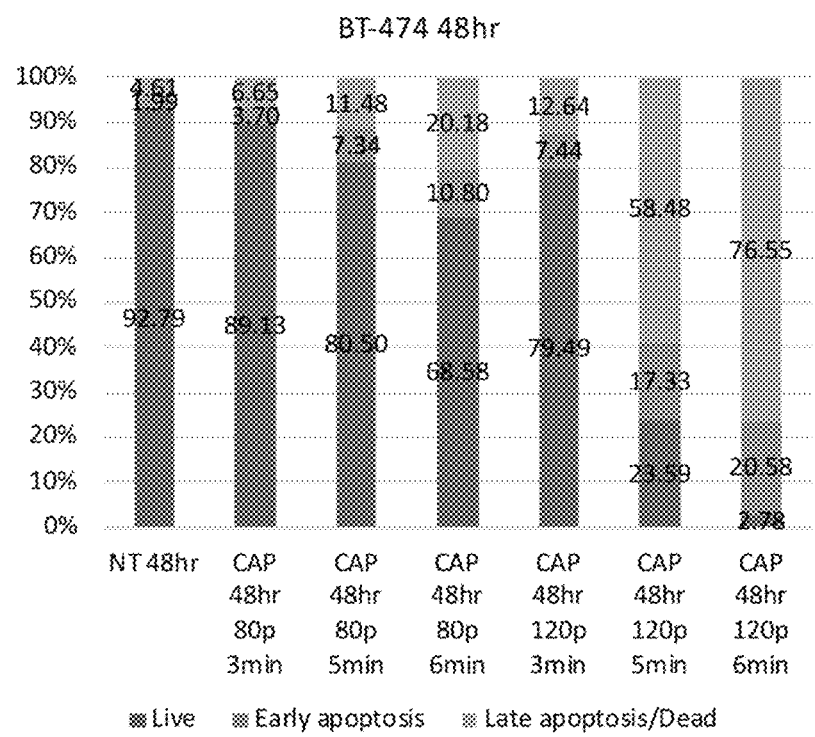
Figure 15A:
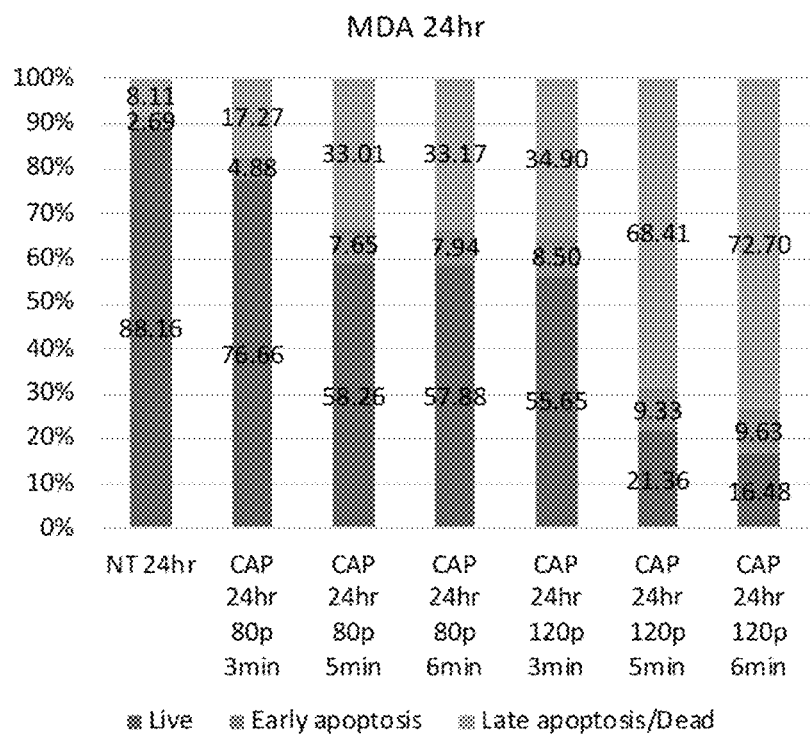
FIGS. 15A-15B show apoptosis analysis of MDA-MB-231 (TN) cell line.
Figure 15B:
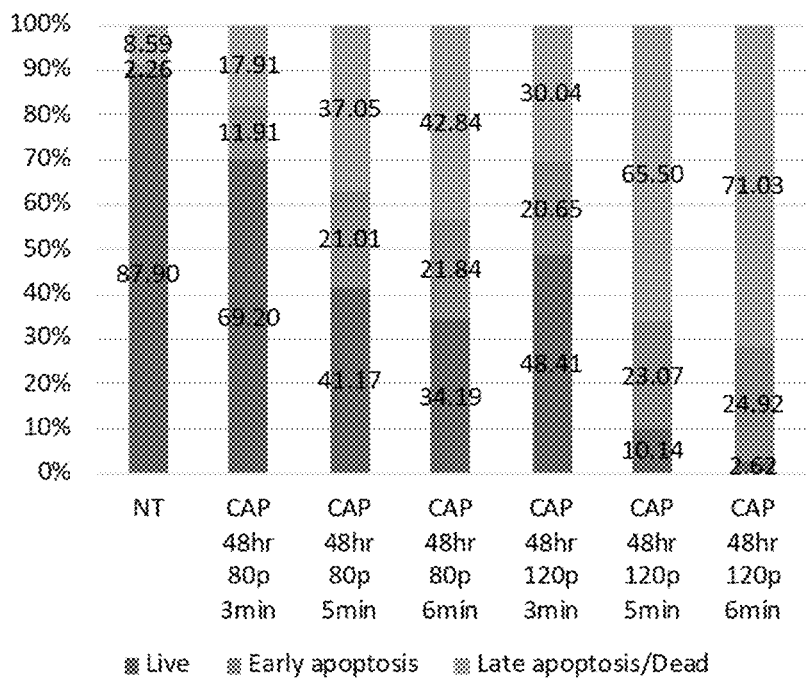
Figure 16A:
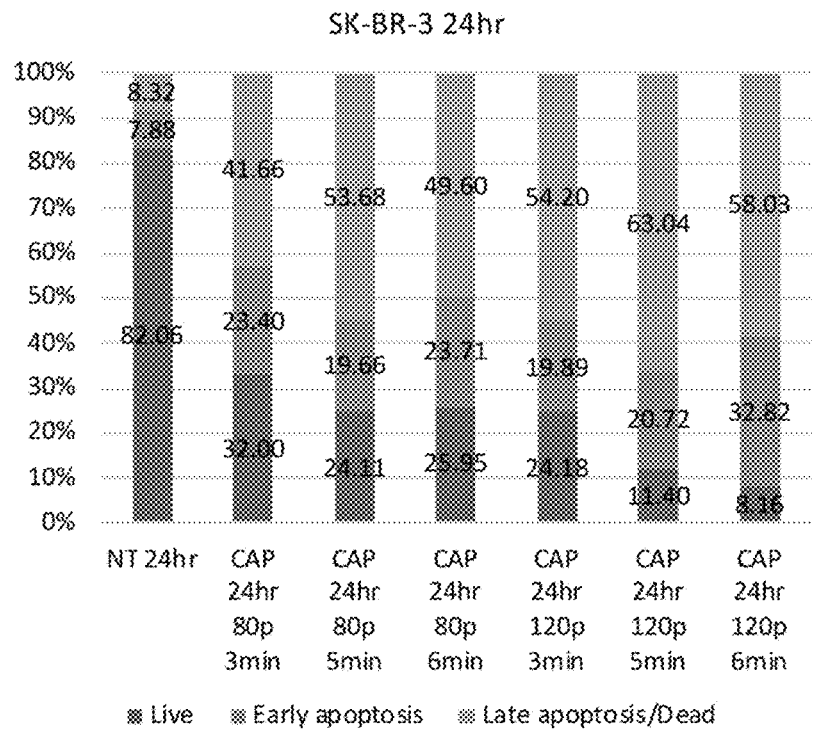
FIGS. 16A-16B show an apoptosis analysis of SK-BR-3 (BERT') cell line.
Figure 16B:
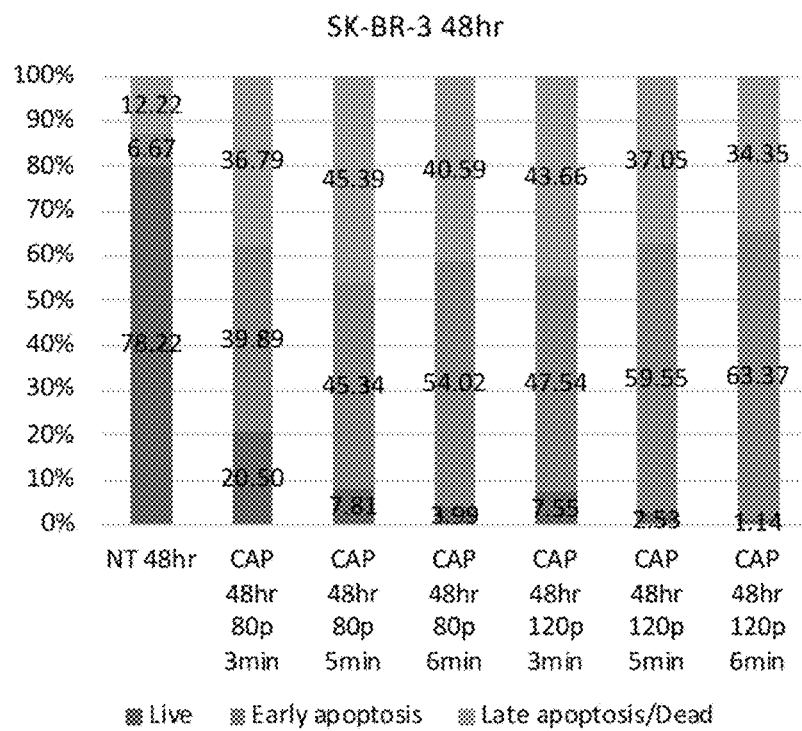

The population of 'Live' cells significantly decreased with increasing treatment power and time compared to No Treatment (p value ranges from <0.05 to <0.001). MCF-7 ($ER^+PR^+HER2^-$) 'Live' population decreased from 80.04% to 2.37% after CAP treatment (FIGS. 13C and 13D); BT-474 ($ER^+PR^+HER2^+$) 'Live' population decreased from 92.11% to 2.78% after CAP treatment (FIGS. 14C and 14D); MDA-MB-231 (TN) 'Live' population decreased from 88.16% to 2.62% after CAP treatment (FIGS. 15C and 15D); SK-BR-3 ($HER2^+$) 'Live' population decreased from 82.06% to 1.14% after CAP treatment (FIGS. 16C and 16D). With increasing treatment power and time, the increase in cells undergoing early apoptosis was seen in all 4 cell lines.

In addition, SK-BR-3 ($HER2^+$) cells were the most susceptible to CAP treatment, and BT-474 ($ER^+PR^+HER2^+$) cells were the most resistance among the 4 cell lines. Strong statistically significant different (*** p<0.001) 'live' population was observed 24 hours post CAP treatment in SK-BR-3 ($HER2^+$) (FIG. 10) with the lowest treatment dosage (80p 3 min). BT-474 ($ER^+PR^+HER2^+$) did not show significant decrease until 24 hours with CAP treatment at 80p for 6 min (* p<0.05, FIG. 14C) or 48 hours with CAP treatment at 80p for 5 min (* p<0.05, FIG. 14D). This finding matches the viability and proliferation inhibition described above.

Comparing the population of 48 hr (FIGS. 7B and 7D to FIG. 10) to 24 hr post CAP treatment (FIGS. 13A and 13C, respectively), CAP-induced apoptosis could take up to 48 hours. For example, at 80p for 3 and 6 min, MCF-7 ($ER^+PR^+HER2^-$) showed an increase in apoptotic cell population from 32.17% to 60.89% 24 hr post CAP treatment; and from 36.95% to 87.30% for 48 hr post CAP treatment, indicating that more cells entered apoptosis procedure between 24 and 48 hours. This phenomenon can be observed in all 4 cell lines for all CAP treatment conditions.

Temporal Progress of Cell Cycle

Stable cell populations for breast cancer cell lines were generated with the IncuCyte® Cell Cycle Green/Red Lentivirus Reagent and treated with CAP for desired dosages. For $HER2^+$ subtype SK-BR-3, a stable cell population could not be generated with the IncuCyte® Cell Cycle Green/Red Lentivirus Reagent. Therefore, anther $HER2^-$ cell line AU-565 was used for cell cycle tracking.

After CAP treatment, cells were monitored in the IncuCyte® for 3 days. Quantification data and phase contrast images for cells in G1 (Red) or S/G2/M (Green) or S to G1 transition (S-G1, Yellow) phases are shown in FIG. 17A to FIG. 19E.

Confluence of 4 stable cell lines after CAP-treatment was consistent with the confluence of non-transfected cell lines (FIGS. 7B-7E) confirmed the cell function was not altered by the lentivirus.

Figure 17A:
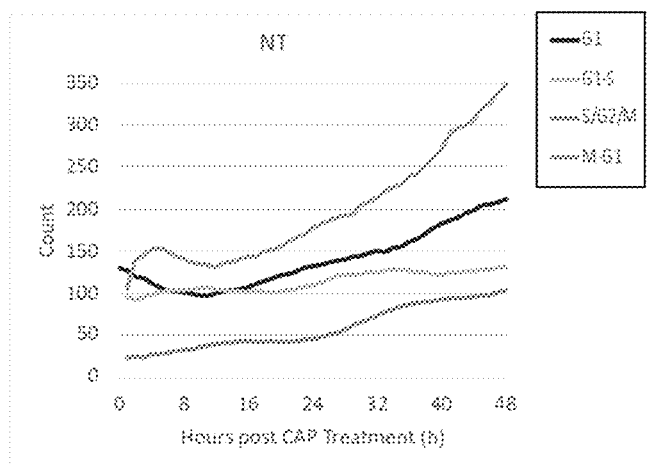
FIGS. 17A-17E show quantification of MCF-7 (ER$^+$PR$^+$HER2$^-$) cells in G1, G1-S, S/G2/M, and M-G1 phases over 72 hours after CAP treatment. A-E) Cells were untreated or treated by CAP with various dosage.
Figure 17B:
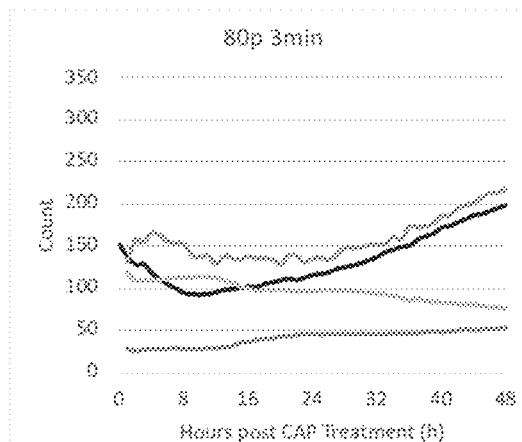
Figure 17C:
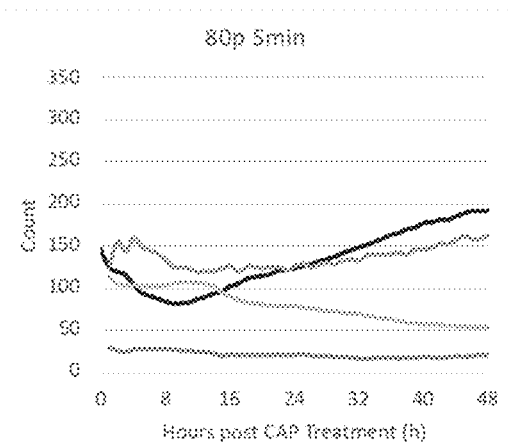
Figure 17D:
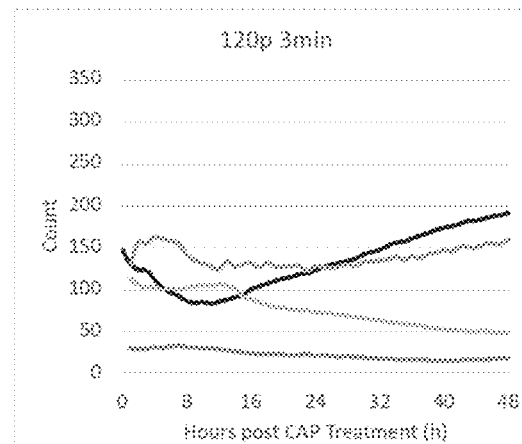
Figure 17E:
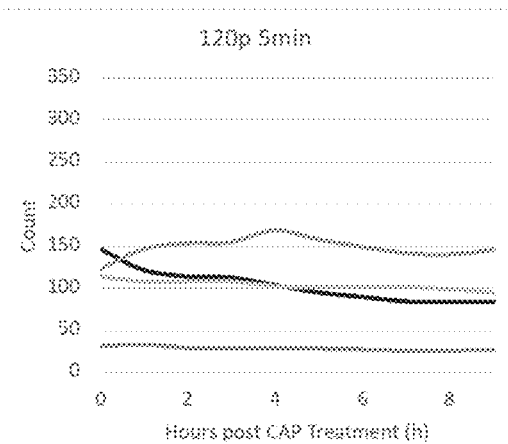
Figure 19A:
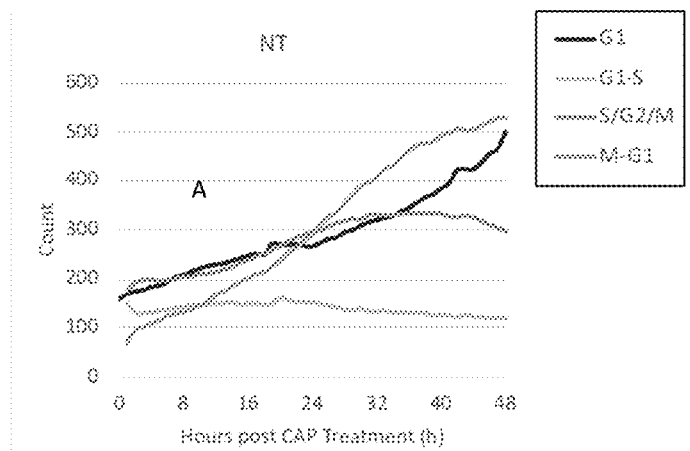
FIGS. 19A-19E show quantification of MDA-MB-231 (TNBC) cells in G1, G1-S, S/G2/M, and M-G1 phases over 72 hours after CAP treatment. A-E) Cells were untreated or treated by CAP with various dosage.
Figure 19B:
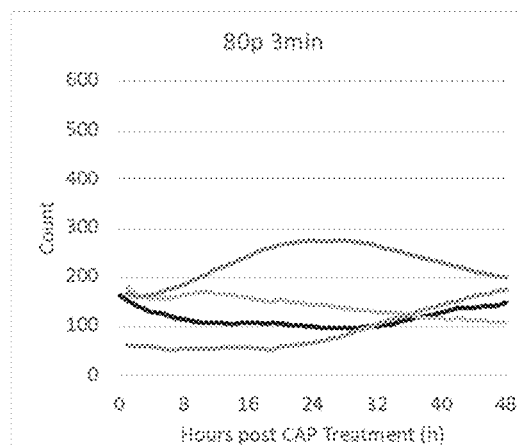
Figure 19C:
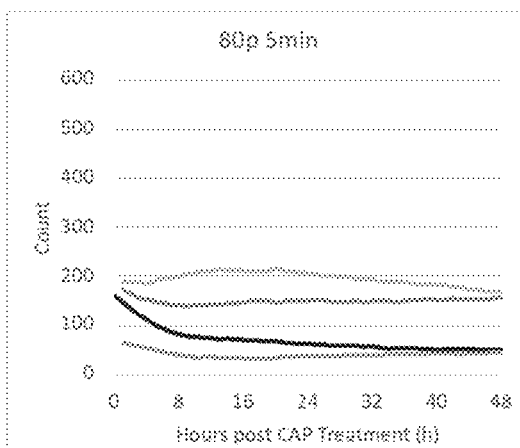
Figure 19D:
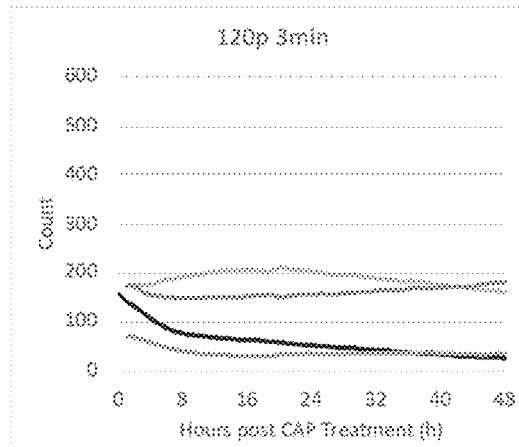
Figure 19E:
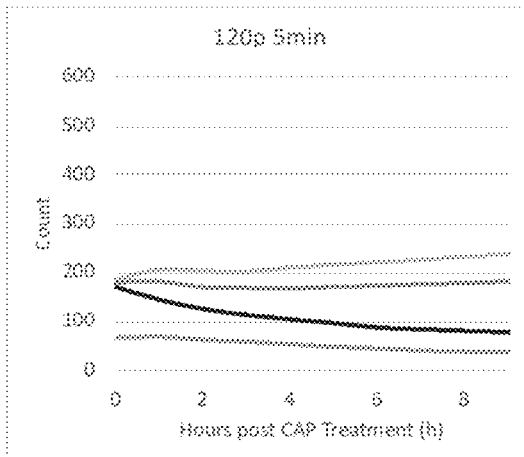
Figure 20A:
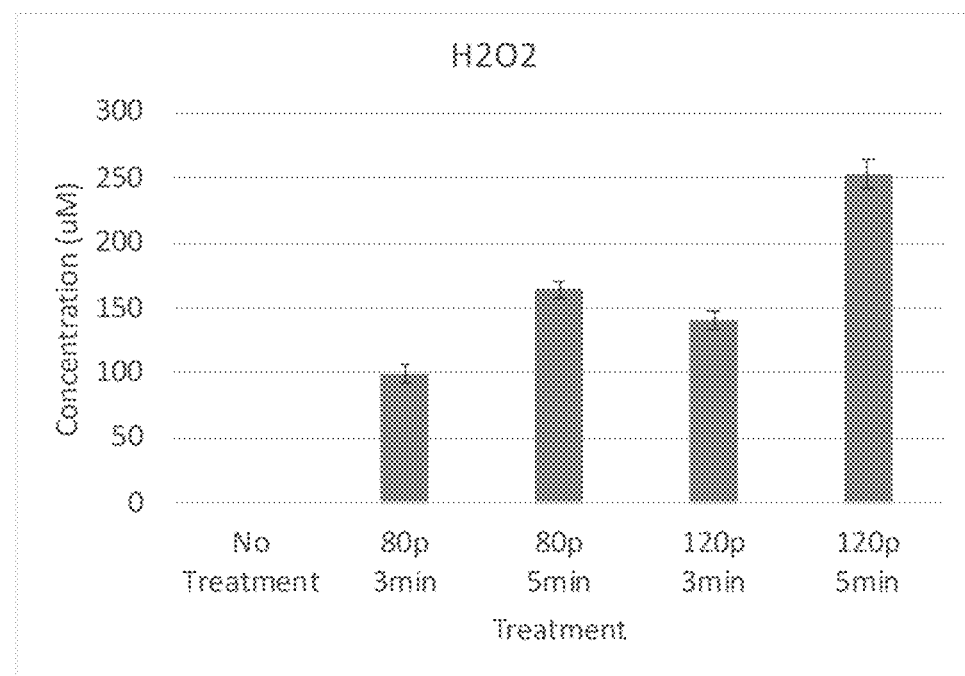
FIGS. 20A-20B show hydroperoxide ($H_2O_2$) and nitrite ($NO_2^-$) measurement with various doses of CAP immediately after treatment. A) Hydroperoxide ($H_2O_2$) concentrations measured in 1 mL of PBS. B) Nitrite ($NO_2^-$) concentrations measured in 1 mL of PBS.
Figure 20B:
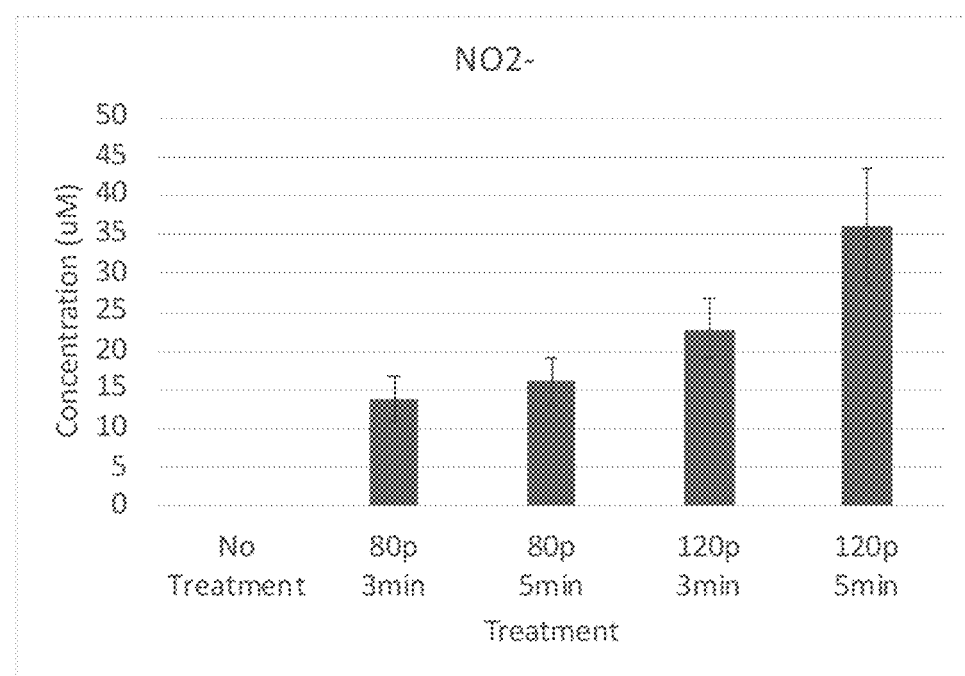

For MCF-7 ($ER^+PR^+HER2^-$) cell line, with low doses of CAP treatment (80p 3 min and 5 min, and 120 3 min), the number of cells in G1-S transition phase and S/G2/M phase showed slight increase first then went down whereas the number of cells in G1 decreased in the first 8 hours post treatment then increased thereafter due to the relative slow growth rate of the cells. When treated with the highest dose of CAP (120 p 5 min), the majority of cells died within 9 hours thus quantification was only plotted for 9 hours (FIG. 17E). The number of cells in all phases decreased.

Low doses of CAP treatment (80 p 3 min and 5 min, and 120 3 min) did not result in significant changes to the cell cycle of BT-474 ($ER^+PR^+HER2^+$), which is in correspondence with the caspase 3/7 activity (FIGS. 12A-12D). With highest CAP dose at 120 p 5 min where apoptosis was observed (FIGS. 12A-12D), the number of cells in G1 decreased whereas G1-S and S/G2/M increased suggesting that cell cycle progressed from G1 to S/G2/M phases.

For MDA-MB-231 (TNBC), low doses of CAP (80 p 3 min and 5 min, 120 p 3 min) decreased the number of cells at G1 phase and cells progressed towards S/G2/M phases (yellow and green). High dose of CAP (120 p 5 min) induced apoptosis immediately thus the number of cells of all phases decreased.

CAP-Generated Reactive Species

Cold atmospheric plasma is a cocktail of reactive species containing electrons, photons, as well as radicals such as hydroxyl radicals, atomic oxygen, singlet oxygen, ozone, nitric oxide, nitrogen dioxide etc. When introduced to the medium in vitro or bodily fluid in vivo these species can form biologically relevant ROS and RNS such as superoxide anion, hydroperoxide, nitrate, nitrite etc. It has been reported that among the many species in the cold plasma cocktail or its activated medium, hydroperoxide ($H_2O_2$) and nitrite ($NO_2^-$) are the long-lived species and have a good chance to reach target cells that are covered by a layer of medium in vitro, or to cross substantial barriers of biological material during treatment in vivo. Bauer, G., "The synergistic effect between hydrogen peroxide and nitrite, two long-lived molecular species from cold atmospheric plasma, triggers tumor cells to induce their own cell death," *Redox Biol* 26, 101291 (2019). These two long-lived species are the major molecules that constitute the CAP-activated medium and contribute to the anti-cancer effect. Yan, D. et al., "Principles of using Cold Atmospheric Plasma Stimulated Media for Cancer Treatment," *Sci Rep* 5, 18339 (2015).

CAP-generated hydroperoxide ($H_2O_2$) and nitrite ($NO_2^-$) were measured in PBS immediately after treatment and their molar concentrations are shown in FIGS. 17A-17E, which suggests that the 'dose' of CAP is dependent on both treatment power and duration. The concentrations of $H_2O_2$ and $NO_2^-$ increasing with power and duration is in correspondence with the apoptosis and cell cycle arrest induced by CAP treatment in a dose-dependent level shown above.

Intracellular Reactive Oxygen Species and Oxidation of RNA

Intracellular oxidative stress for 4 breast cancer cell lines was monitored for up to 48 hours post CAP treatment. Although both are reactive oxygen sources, CAP and $H_2O_2$ treatment resulted in completely different response in cells. Cells treated with $H_2O_2$ treatment as positive control showed immediate intracellular oxidative stress within 1 hour of treatment, while CAP treated cells did not generate intracellular ROS within 6 hours. The intensity of intracellular ROS of $H_2O_2$ treated cells did not change over 48 hours after treatment, whereas the ROS within CAP-treated cells gradually increased over time and plateaued after 24 hours.

DISCUSSION

In the past decade, studies on a variety of tumor cell types have been published using different CAP devices. CAP has been previously demonstrated as a promising anti-cancer treatment for renal adenocarcinoma, colorectal carcinoma, ovarian adenocarcinoma, pancreatic adenocarcinoma, esophageal adenocarcinoma, and triple-negative breast cancer. Molecular features and corresponding tumor subtypes of each cell line for 84 breast cancer cell lines were sorted out by Dai et al. ("Breast Cancer Cell Line Classification and Its Relevance with Breast Tumor Subtyping," *J Cancer* 8, 3131-3141 (2017)), who concluded that breast tumor cell lines are feasible but crude models for tumors of the same subtype although having a high mutational frequency. The present experiments are the first to analyze dose-dependent apoptotic effect of CAP on breast cancer cell lines based on molecular subtypes.

Ki-67 expression is an independent prognostic parameter according to breast cancer molecular subtypes in breast cancer patients. Soliman, et al., "Ki-67 as a prognostic marker according to breast cancer molecular subtype," *Cancer Biol Med* 13, 496-504 (2016). It is frequently determined in routine clinical work based on the data from a large cohort of a clinical cancer registry. Inwald, E. C. et al., "Ki-67 is a prognostic parameter in breast cancer patients: results of a large population-based cohort of a cancer registry," *Breast Cancer Res Treat* 139, 539-552 (2013). Soliman et al. analyzed the relationship of Ki-67 index with clinicopathological factors in 107 cases of breast cancer as well as with prognosis based on breast cancer molecular subtypes. Their results indicate that patients with Ki-67 expression higher than 15% exhibited higher incidence of metastasis and recurrence than those with Ki-67 less than 15% (p=0.000). Cabrera-Galeana et al. reported their findings that patients without a decrease in Ki-67 in residual tumors after neoadjuvant-chemotherapy had poor prognosis. Cabrera-Galeana, P. et al., "Ki67 Changes Identify Worse Outcomes in Residual Breast Cancer Tumors After Neoadjuvant Chemotherapy. *Oncologist* 23, 670-678, doi:10.1634/theoncologist.2017-0396 (2018) Ki67 decrease significantly correlated with better disease-free survival and overall survival compared with no decrease, particularly in the luminal B subgroup. Nonreduction of Ki-67 significantly increased the hazard ratio of recurrence and death by 3.39 (95% confidence interval [CI] 1.8-6.37) and 7.03 (95% CI 2.6-18.7), respectively. These studies suggest that new therapeutic strategies that can reduce Ki67 expression are warranted.

At molecular level, expression and localization of Ki-67 is associated with cell cycle. Phosphorylation and dephosphorylation of the Ki-67 protein are controlled by key regulatory structures of the cell cycle and occur within the cell cycle[64]. Endl, E. & Gerdes, J., "Posttranslational Modifications of the Ki-67 Protein Coincide With Two Major Checkpoints During Mitosis," *Journal of Cellular Physiology* 182, 371-3880 (2000). During early G1, the Ki-67 antigen is detected at a large number of discrete foci throughout the nucleoplasma, extending to the nuclear envelope. During S-phase and G2, the antigen is located in the nucleolus. Kill, I. R., "Localisation of the Ki-67 antigen within the nucleolus. Evidence for a fibrillarin-deficient region of the dense fibrillar component," *Journal of cell science* 109, 1253-1263 (1996). After quantifying and characterizing the expression level of Ki-67 as a function of cell cycle, Chierico et al. found that it is regulated differently in non-cancerous and cancerous cells, providing an insight for the mechanism of CAP selectivity towards cancerous cells. Chierico, L. et al., "The role of the two splice variants and extranuclear pathway on Ki-67 regulation in non-cancer and cancer cells," *PLoS One* 12 (2017). The present experiments of Ki-67 expression for the 4 breast cancer subtypes indicates the downregulation of Ki-67 by CAP with slightly different dosages.

Apoptosis, a programmed cell death, induced by CAP treatment could be achieved from its reactive species-mediated oxidative stress in the mitochondria. The increased mitochondrial transmembrane potential and the release of pro-apoptotic factors after CAP treatment are the key factors for apoptosis. Ahn, H. J. et al., "Atmospheric-pressure plasma jet induces apoptosis involving mitochondria via generation of free radicals," *PLoS One* 6 (2011). This process is regulated by the Bcl-2 protein family and leads to the activation of the caspase cascade. Apoptosis assay by flow cytometry and by IncuCyte demonstrated the process of apoptosis for each cell line quantitatively and visually. Cells enter apoptosis in a dose-dependent manner. Apoptosis was seen earlier in the cells treated with higher CAP treatment power and time.

The present experiments have shown that different molecular subtypes of breast cancer demonstrate differing tolerance to CAP treatment. Additionally, HER2[+] cell lines showed a more sensitive response while BT-474 (ER[+]PR[+] HER2[+]) was the most resistant to CAP treatment.

Cell cycle analysis after CAP treatment revealed a significant decrease in the number of cells at G1 with higher number of cells that were in S/G2/M phase with strong CAP dosage when apoptosis activity was induced.

Cold atmospheric plasma and its anti-cancer effects have been reported repeatedly over the last two decades. However, the mechanism of CAP induce cell death in malignant cells rather than normal cells was not yet established.

Molecular pathways of metastasis across 3 breast carcinoma subtypes including hormone[+], TNBC, and HER2[+] have been studied using a proteomic approach. They suggested that hormone[+]breast cancer shared similarities with TNBC cells, whereas HER2+ cells specifically changed their molecular phenotype resulting in highest metastatic potential.

CONCLUSION

CAP as an effective treatment for all breast cancer subtypes, and the required dosage can be optimized based on receptor status. Due to the ubiquitous expression in all proliferating cells, Ki-67 could be a potential therapeutic target in cancer, in addition to being a prognostic marker. Inactivation of Ki-67 could be a promising strategy for the treatment not only for breast cancer but also of other cancer types.

EXPERIMENTS

Methods and Materials
Cold Plasma Device

CAP was generated by the Canady Cold Plasma Conversion System (CCPCS), which was reported in Cheng, X. et al., "Treatment of Triple-Negative Breast Cancer Cells with the Canady Cold Plasma Conversion System: Preliminary Results,". *Plasma* 1, 218-228, (2018). CCPCS parameters were set as follows: helium flow rate at 3 L/min; power settings at 80p (15.7 W), 100p (22.3 W), and 120p (28.7 W).
Cell Culture and Viability Assay Cell Culture.

Human breast ductal carcinoma BT-474 and breast adenocarcinoma SK-BR-3 and AU-565 were purchased from ATCC (Manassas, Va., USA) and cultured according to provided protocol. Human adenocarcinoma cell lines MCF-7 and MDA-MB-231 were generously donated by Professor Kanaan's laboratory at Howard University. SK-BR-3 was cultured with McCoy's 5A and BT-474, MCF-7, MDA-MB-231, and AU-565 were culture with RPMI 1640 medium supplemented with 10% fetal bovine serum (FBS) (Sigma-Aldrich, St. Louis, Mo., USA) and 1% Pen Strep (Cat. #15140163, Thermo Fisher Scientific, Waltham, Mass., USA). All cell lines were cultured in a 37° C. and 5% $CO_2$ humidified incubator (Thermo Fisher Scientific, Waltham, Mass., USA). When reaching approximately 80% confluence, cells were seeded at a concentration of $10^5$ cells/well into 12-well plates (USA Scientific, Ocala, Fla., USA) with 1 mL culture media per well for all assays.

Cell Viability Assay.

Thiazolyl blue tetrazolium bromide (MTT) was purchased from Abcam (Cat. #ab146345) and viability assays were carried out after 48 hr CAP treatment according to the manufacturer's protocol. Briefly, cell culture media were replaced with MTT solution and incubated for 3 hours in a 37° C. and 5% $CO_2$ humidified incubator. MTT solution was then replaced with MTT solvent and read with a BioTek Synergy HTX (Winooski, Vt., USA) microplate reader at 570 nm absorbance.
IncuCyte Live Cell Imaging for Caspase Activity and Cell Cycle Caspase 3/7 Activity.

The IncuCyte® Caspase-3/7 Dyes for Apoptosis (Cat. #4440, IncuCyte) couple the activated caspase-3/7 recognition motif (DEVD) to a DNA intercalating dye and are ideally suited to the mix-and-read, real-time quantification of cells undergoing caspase-3/7 mediated apoptosis. Addition of the IncuCyte® Caspase-3/7 Dyes to normal healthy cells is non-perturbing to cell growth and morphology. When added to tissue culture medium, the inert, non-fluorescent substrate crosses the cell membrane where it is cleaved by activated Caspase-3/7 resulting in the release of the DNA dye and fluorescent staining of the nuclear DNA.

Breast cancer cells were seeded in 12-well plates at a density of $10^5$ cells/well, treated or untreated with CAP, followed by staining with IncuCyte Caspase 3/7 dye. Then the cells were placed in IncuCyte and scanned with phase contrast and green channels at 10× magnification at an interval of 1 h for 3 days. After scanning, fluorescent object were quantified using the IncuCyte integrated analysis software with background subtraction.

Cell Cycle Tracking.

The IncuCyte® Cell Cycle Green/Red Lentivirus Reagent (Cat. #4779, IncuCyte) is a fluorescent, single cassette indicator expressing both the GFP (green fluorescent protein) and mKate2 (red fluorescent protein) to distinguish between cells in the G1 and S/G2/M cell cycle phase without altering cell function. Stable cell populations for MCF-7, BT-474, MDA-MB-231, and AU-565 cell lines were generated using puromycin selection. Stable cells were seeded in 12-well plates at a density of $10^5$ cells/well, treated or untreated with CAP and placed in IncuCyte for 3-day scanning. Cells were scanned every hour with phase contrast, green, and red channels at 10× magnification with Cell by Cell Module for MCF-7 and MDA-MBA-231 cells. For BT-474 cells, which tend to grow in clusters, Cell by Cell Module could not properly detect the boundaries between each cell, basic scanning and analysis was used.
Flow Cytometry Apoptosis assays were carried out on all 4 breast cancer cell lines with FITC Annexin V (Cat. #556419, BD Biosciences) and PI (ThermoFisher, Cat. #P3566) by flow cytometry. Cells were seeded in 12-well plates and treated with CAP for various dosage. After incubated with desired periods of time, cell culture media was removed, and the cells were washed twice with PBS and detached with 250 µl of trypsin-EDTA (Sigma-Aldrich, Cat. #T4049). Please note that the culture media, the PBS for washing, as well as the trypsin-EDTA were all collected and spun down for apoptotic staining and analysis. Plotting of the data and analysis of the results were performed with FCS Express 7 (De Novo Software).
Confocal Microscopy Immunofluorescent Staining and Imaging.

Round cover glass (12 mm diameter, Fisher Scientific, Cat. #50-192-8952) were placed in 12-well plates and coated with fibronectin (Sigma-Aldrich, Cat. # F1141) and collagen I (ThermoFisher, Cat. #A1064401) for at least 1 hour prior to seeding cells. Seeding cells on cover slides in 12-well plates instead of chamber slides can produce consistent CAP treatment effect with various dosage since the well size and cell number remained the same as the viability assay by MTT and apoptosis assay by flow cytometry. After CAP treatment and desired periods of incubation time, cells were stained with Alexa Fluor 488 conjugated Ki-67 Rabbit mAb (Cell Signaling Technology, Cat. #11882) according to manufacturer's protocol. Briefly, cells were washed with phosphate buffered saline (PBS) and fixed with cold anhydrous methanol (pre-cooled in −80 C freezer) for 10 min at room temperature. After the methanol was aspirated, cells were washed twice with PBS and blocked in blocking buffer for 60 min. Then, Ki-67 and Isotype control (Cell Signaling Technology, Cat. #4340) antibodies were diluted with 1:200 dilution with antibody dilution buffer and 400 µl of which was added to designated wells. Cells were incubated overnight at 4 C refrigerator protected from light. Round cover slides with cells were washed twice before they were carefully moved onto 1"×3"×1 mm microscope slides. The cells were first covered with Antifade Mounting Reagent with DAPI (Vector Laboratories, Cat. # H-1500) drops and then a 24×50 mm cover glass (Cancer Diagnostics, Cat. # GC2450-ACS), and allowed to cure for up to 2 nights in the 4 C refrigerator.

Cells were imaged with a 63× lens on a LSM 510 (Carl Zeiss) with 405 and 488 nm laser bands.

Intensity Quantification.

The intensity of Ki-67 expression was quantified using Zen Lite 3.1 from Zeiss. Nuclei were outlined with Spline Contour tool in each image (image size: 108.36 µm×108.36 µm, scale bar 50 µm). The average intensity of Ki-67 staining of each nucleus within the outline was measured by Zen Lite 3.1 and exported to and plot by Microsoft Excel. Five images were analyzed for each condition, and in the cases when there were no cells remaining after the CAP treatment, the cell count was recorded as 0.

CAP-Generated Species Measurement

To measure the concentrated of hydrogen peroxide ($H_2O_2$) and nitrate ($NO_2^-$) generated by CAP, 1 mL of PBS was added to the wells of a 12-well plate and treated by CAP with desired dosage. $H_2O_2$ and $NO_2^-$ were measured immediately with Peroxide Assay Kit (Cat. # MAK311, Sigma-Aldrich) and Griess Reagent System (Cat. # G2930) respectively.

Statistics

All assays were repeated at least 3 times and data was plotted by Microsoft Excel 2016 as the mean±standard error of the mean. Student t test was used to check statistical significance where applicable. The differences were considered statistically significant for $*p<0.05$, $p<0.01$, and $*p<0.001$.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A method for performing cold atmospheric plasma therapy to treat cancer in a patient, the method comprising:
    creating a database of cancer cell lines in a data storage;
    associating with each cancer cell line in said database cold atmospheric plasma settings producing in each said cancer cell line degradation of Histone RNA during S-phase induced by oxidation of RNA;
    selecting on a graphical user interface of a cold atmospheric plasma generator a target cancer cell line to be treated;
    selecting with a processor in said cold atmospheric plasma generator cold atmospheric plasma settings associated with said target cancer cell line in said database stored in said data storage; and
    applying cold atmospheric plasma with said cold atmospheric plasma generator at said selected cold atmospheric pressure settings to said target cancer cells.

2. A method for performing cold atmospheric plasma therapy to treat cancer according to claim 1 wherein the cancer comprises breast cancer.

3. A method for performing cold atmospheric plasma therapy to treat cancer according to claim 1 wherein said data storage comprising a memory in said cold atmospheric plasma generator.

4. A method for performing cold atmospheric plasma therapy to treat cancer according to claim 1 wherein cold atmospheric plasma comprises plasma below 35° C.

5. A method for performing cold atmospheric plasma therapy to treat cancer according to claim 4 wherein the cancer comprises breast cancer.

6. A method for performing cold atmospheric plasma therapy to treat cancer according to claim 4 wherein said data storage comprising a memory in said cold atmospheric plasma generator.

7. A method for performing cold atmospheric plasma therapy to treat cancer according to claim 4 wherein said resecting target cancer cells comprises completely resecting a cancerous tumor.

8. A method for performing cold atmospheric plasma therapy to treat cancer according to claim 5 wherein cold atmospheric plasma comprises plasma below 35° C.

9. A method for performing cold atmospheric plasma therapy to treat cancer in a patient using a cold atmospheric plasma generator and a database of cancer cell lines and cold atmospheric plasma settings for producing in each said cancer cell line degradation of Histone RNA during S-phase induced by oxidation of RNA, the method comprising:
    resecting target cancer cells from a patient;
    selecting on a graphical user interface of said cold atmospheric plasma generator a target cancer cell line to be treated;
    in response to said selecting of a target cancer cell line, configuring said cold atmospheric plasma generator with a processor to treat tissue on a periphery of said resected target cancer cells using cold atmospheric plasma settings associated in said database with said target cancer cell line; and
    applying cold atmospheric plasma with said cold atmospheric plasma generator at said selected cold atmospheric pressure settings to said target cancer cells.

* * * * *